United States Patent
Farmer et al.

(10) Patent No.: US 9,192,659 B2
(45) Date of Patent: *Nov. 24, 2015

(54) INACTIVATED BACTERIAL CELL FORMULATION

(71) Applicant: Ganeden Biotech, Inc., Mayfield Heights, OH (US)

(72) Inventors: Sean Farmer, Miami, FL (US); Michael A. Bush, Brecksville, OH (US); David Keller, Beachwood, OH (US)

(73) Assignee: Ganeden Biotech, Inc., Mayfield Heights, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/064,863

(22) Filed: Oct. 28, 2013

(65) Prior Publication Data

US 2014/0050764 A1     Feb. 20, 2014

Related U.S. Application Data

(63) Continuation of application No. 12/770,457, filed on Apr. 29, 2010, now Pat. No. 8,568,743.

(60) Provisional application No. 61/285,255, filed on Dec. 10, 2009, provisional application No. 61/214,876, filed on Apr. 29, 2009.

(51) Int. Cl.
*A61K 39/07* (2006.01)
*A61K 35/74* (2015.01)
*A61K 35/742* (2015.01)

(52) U.S. Cl.
CPC ............. *A61K 39/07* (2013.01); *A61K 35/74* (2013.01); *A61K 35/742* (2013.01)

(58) Field of Classification Search
None
See application file for complete search history.

(56) References Cited

U.S. PATENT DOCUMENTS

| | | |
|---|---|---|
| 6,461,607 B1 | 10/2002 | Farmer |
| 6,733,751 B2 | 5/2004 | Farmer |
| 6,849,256 B1 | 2/2005 | Farmer |
| 6,905,692 B2 | 6/2005 | Farmer |
| 7,374,753 B1 | 5/2008 | Farmer et al. |
| 7,507,402 B1 | 3/2009 | Farmer et al. |
| 7,708,988 B2 | 5/2010 | Farmer |
| 7,807,151 B2 | 10/2010 | Farmer |
| 8,097,247 B2 | 1/2012 | Farmer |
| 8,187,590 B2 | 5/2012 | Farmer |
| 2006/0099197 A1 | 5/2006 | Farmer |

FOREIGN PATENT DOCUMENTS

| | | |
|---|---|---|
| JP | 2008013543 A | 1/2008 |
| WO | WO-0010582 A2 | 3/2000 |
| WO | 0113927 A2 | 3/2001 |
| WO | 0134168 A1 | 5/2001 |

OTHER PUBLICATIONS

Araki et al. "Occurrence of N-Nonsubstituted Glucosamine Residues in Peptidoglycan of Lysozyme-Resistant Cell Walls from *Bacillus cereus*." *J. Biol. Chem.* 247.19(1972):6312-6322.
ATCC Catalogue of Bacteria and Bacteriophages, Accession No. 31284, retrieved Aug. 11, 2009.
Baron. "Original Research: A Patented Strain of *Bacillus coagulans* Increased Immune Response to Viral Challenge." *Postgrad. Med.* 121.2(2009):114-118.
Castellazzi et al. "In vitro Activation of Mononuclear Cells by Two Probiotics: *Lactobacillus paracasei* I 1688, *Lactobacillus salivarius* I 1794, and their Mixture (PSMIX)." *Immunological Invest.* 36.4(2007):413-421.
Christi et al. "Role of Dietary Sulphate in the Regulation of Methanogenesis in the Human Large Intestine." *Gut.* 33(1992):1234-1238.
Clausen et al. "Functional Significance of the Activation-Associated Receptors CD25 and CD69 on Human NK-Cells and NK-like T-Cells." *Immunobiol.* 207.2(2003):85-93.
Cross et al. "Patterns of Cytokine Induction by Gram-Positive and Gram-Negative Probiotic Bacteria." *FEMS Immunol. Med. Microbiol.* 42.2(2004):173-180.
de Vrese et al. "Probiotic Bacteria Reduced Duration and Severity but not the Incidence of Common Cold Episodes in a Double Blind, Randomized, Controlled Trial." *Vaccine.* 24(2006):6670-6674.
Flinterman et al. "Probiotics Have a Different Immunomodulatory Potential in vitro versus ex vivo Upon Oral Administration in Children With Food Allergy." *Intl. Arch. Allergy Immunol.* 143.3(2007):237-244.
Gibson et al. "Selective Stimulation of Bifidobacteria in the Human Colon by Oligofructose and Insulin." *Gastroenterol.* 108.4(1995):975-982.
Hun. "Original Research: *Bacillus coagulans* Significantly Improved Abdominal Pain and Bloating in Patients with IBS." *Postgrad. Med.* 121.2(2009):119-124.
Jensen et al. "An Antiinflammatory Immunogen From Yeast Culture Induces Activation and Alters Chemokine Receptor Expression on Human Natural Killer Cells and B Lymphocytes in vitro." *Nutr. Res.* 27.6(2007):327-335.

(Continued)

*Primary Examiner* — Brian J Gangle
(74) *Attorney, Agent, or Firm* — Mintz Levin Cohn Ferris Glovsky and Popeo P.C.; Ingrid A. Beattie

(57) ABSTRACT

The invention relates to the use of lactic acid-producing bacteria to boost the immune system.

15 Claims, 22 Drawing Sheets

(56) References Cited

OTHER PUBLICATIONS

Jensen et al. "GanedenBC30™ Cell Wall and Metabolites: Anti-Inflammatory and Immune Modulating Effects in vitro." *BMC Immunol.* 11(2010):15.

Kaya et al. "Structural Studies on the Linkage Unit Between Poly(galactosylglycerol phosphate) and Peptidoglycan in Cell Walls of *Bacillus coagulans*." *Eur. J. Biochem.* 147(1985):41-46.

Ng et al. "Mechanisms of Action of Probiotics: Recent Advances." *Inflammatory Bowel Dis.* 15.2(2009):300-310.

Panda et al. "Effect of Probiotic (*Lactobacillus sporogenes*) Feeding on Egg Production and Quality, Yolk Cholesterol and Humoral Immune Response of White Leghorn Layer Breeders." *J. Sci. Food Agricul.* 88.1(2008):43-47.

Zhou et al. "Effect of Treatment With Probiotics as Water Additives on Tilapia (*Oreochromis niloticus*) Growth Performance and Immune Response." *Fish Physiol. Biochem.* 36.3(2009):501-509.

Riazi, S. et al., "Characterization of lactosporin, a novel antimicrobial protein produced by Bacillus coagulans ATCC 7050," J. Appl. Microbiol., vol. 106.4 (2009):1370-1377.

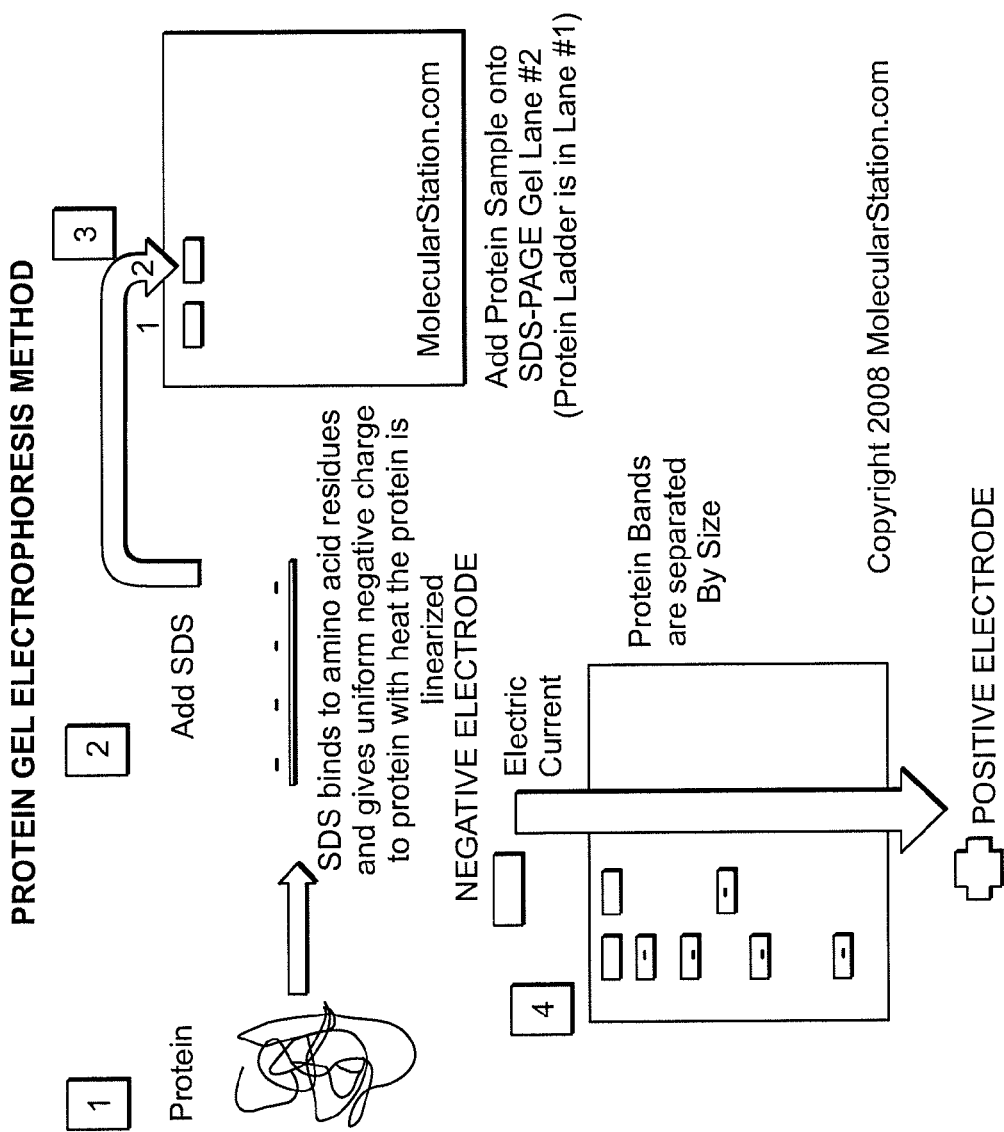

INACTIVATED BACTERIAL CELL FORMULATION

RELATED APPLICATIONS

This application is a continuation application of U.S. Ser. No. 12/770,457, filed on Apr. 29, 2010, allowed, which claims priority to U.S. Ser. No. 61/214,876, filed on Apr. 29, 2009 and U.S. Ser. No. 61/285,255, filed on Dec. 10, 2009, each of which is herein incorporated by reference in their entirety.

FIELD OF THE INVENTION

The invention relates to the use of viable and non-viable bacteria to boost the immune system.

BACKGROUND OF THE INVENTION

The gastrointestinal microflora plays a number of vital roles in maintaining gastrointestinal tract function and overall physiological health. The growth and metabolism of the many individual bacterial species inhabiting the gastrointestinal tract depend primarily upon the substrates available to them, most of which are derived from the diet. See, e.g., Gibson G. R. et al., 1995 Gastroenterology 106: 975-982; Christl, S. U. et al., 1992 Gut 33: 1234-1238. These findings have led to attempts to modify the composition and metabolic activities of the bacterial community through diet, primarily with probiotics, which are live microbial food supplements.

Probiotic organisms are non-pathogenic, non-toxigenic, retain viability during storage, and typically survive passage through the stomach and small intestine. Since probiotics do not generally permanently colonize the host, they need to be ingested regularly for any health promoting properties to persist.

SUMMARY OF THE INVENTION

The invention describes the use of lactic acid-producing bacteria or non-viable fragments or products thereof to boost the immune system. Specifically, the administration of *Bacillus coagulans*, purified cell wall components of *Bacillus coagulans*, or culture supernatants of *Bacillus coagulans* increases the immune system's ability to fight pathogens. Cell wall components and/or culture supernatants are useful in products where conditions are not optimal for long-term vegetative cell viability, e.g., shelf stable beverages or food compositions. Alternatively, inactivated/dead *Bacillus coagulans*, e.g., heat killed *Bacillus coagulans* is administered to boost the immune system. The methods optionally include administration of purified viable *Bacillus coagulans* vegetative cells and/or spores to boost the immune system.

Accordingly, a method of enhancing or boosting an immune response to a microbial pathogen is carried out by identifying a subject infected with a microbial pathogen and administering to the subject a composition comprising a viable *Bacillus coagulans* bacterium, a non-viable fragment of the bacterium, or a non-viable extracellular product of the bacterium. The bacteria, fragments, or products are administered in an amount that enhances the immune response of the subject to the pathogen with which the subject is infected. Preferably, the bacteria, fragments, or products are purified or fractionated from other bacteria or other components of the bacteria (in the case of fragments, e.g., cell wall fragments or secreted products).

Purified and/or isolated *Bacillus coagulans* is particularly useful as a probiotic in the methods and compositions described herein. By "purified" or "substantially purified" is meant a *Bacillus coagulans* bacterium, a non-viable fragment of the bacterium, or a non-viable extracellular product of the bacterium that is substantially free of contaminating microorganisms or other macromolecules, e.g., polysaccharides, nucleic acids, or proteins. A purified preparation contains at least 75%, 85%, 95% or 100% of the desired composition and is substantially free of other sub-cellular components such as cytoplasmic organelles. For example, a bacterial cell wall fraction is at least 75%, 80%, 85%, 90%, 95%, 98%, 99%, or 100% cell wall fragments. Such a preparation is sustainably free of cytoplasm intracellular organelles and secreted bacterial products.

In one aspect, the microbial pathogen is a bacterium or virus such as a pathogen that causes a respiratory infection. For example, the pathogen comprises an influenza virus such as a human, avian, or swine influenza virus or combination thereof. Other viral pathogens include adenovirus.

The compositions of the invention comprise an immune-enhancing amount of a viable *Bacillus coagulans* bacterium, a non-viable fragment of *Bacillus coagulans* bacterium, or a non-viable extracellular product of *Bacillus coagulans* bacterium (e.g., a supernatant of a *Bacillus coagulans* bacterium). Enhancement of the immune response comprises an increase in cytokine (e.g., interleukin-2 (IL-2), IL-4, IL-6, IL-10, tumor necrosis factor-$\alpha$ (TNF-$\alpha$), and interferon-$\gamma$ (IFN-$\gamma$) production or an increase in immune cell migration to an infection site. Immune enhancement also includes boosting the immune system by increasing cytokine production, activating the immune surveillance aspect of polymorphonuclear leukocytes (PMN), increasing immune cell chemotaxis, activating NK cells, and/or increasing monocyte phagocytosis. Specifically, the compositions of the invention increase the chemotactic abilities and phagocytic abilities of PMNs. The compositions of the invention also increase the expression of CD69 on NK cells.

In one aspect, an immune-enhancing amount of *Bacillus coagulans*, *Bacillus coagulans* supernatant, or *Bacillus coagulans* cell wall components is about 0.1 mg to about 10 grams, e.g., about 1 mg to about 10 grams, about 10 mg to about 5 grams; about 100 mg to about 1 gram; or about 200 mg to about 1 gram.

Also within the invention are compositions suitable for human ingestion, such as a composition comprising a purified cell wall of a *Bacillus coagulans* bacterium or a composition comprising a dried or lyophilized secreted product or mixture of secreted products of *Bacillus coagulans*. Exemplary formulations include a pill, capsule, or suspension.

Exemplary bacterial species for the compositions and methods described herein include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20 (GB-20), ATCC Designation Number PTA-6085; GBI-30 (GB-30/Ganeden BC$^{30}$™/BC$^{30}$), ATCC Designation Number PTA-6086; and GBI-40 (GB-40), ATCC Designation Number PTA-6087; see, U.S. Pat. No. 6,849,256 to Farmer). Preferably, the *Bacillus coagulans* comprises GBI-30 (BC$^{30}$), or any strain of the organism described in U.S. Ser. No. 11/706,642, hereby incorporated by reference.

The *Bacillus coagulans* Hammer strains of the invention are non-pathogenic and generally regarded as safe for use in human nutrition (i.e., GRAS classification) by the U.S. Federal Drug Administration (FDA) and the U.S. Department of Agriculture (USDA), and by those skilled in the art. Furthermore, the *Bacillus coagulans* Hammer strains of the invention germinate at or below human body temperature, rendering them useful as probiotics. Many *Bacillus coagulans* strains outside the Hammer group have mostly industrial applications, little or no nutritional benefit, and environmental contaminants that have not been evaluated for safety. Moreover, many other non-Hammer strains of *Bacillus coagulans* grow optimally at temperatures that exceed human body temperature and, thus, do not germinate efficiently in the human body. Such strains are less or not suitable as probiotics for human consumption.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 31 is an illustration of a typical protein gel electrophoresis method.

DETAILED DESCRIPTION

Figure 1:
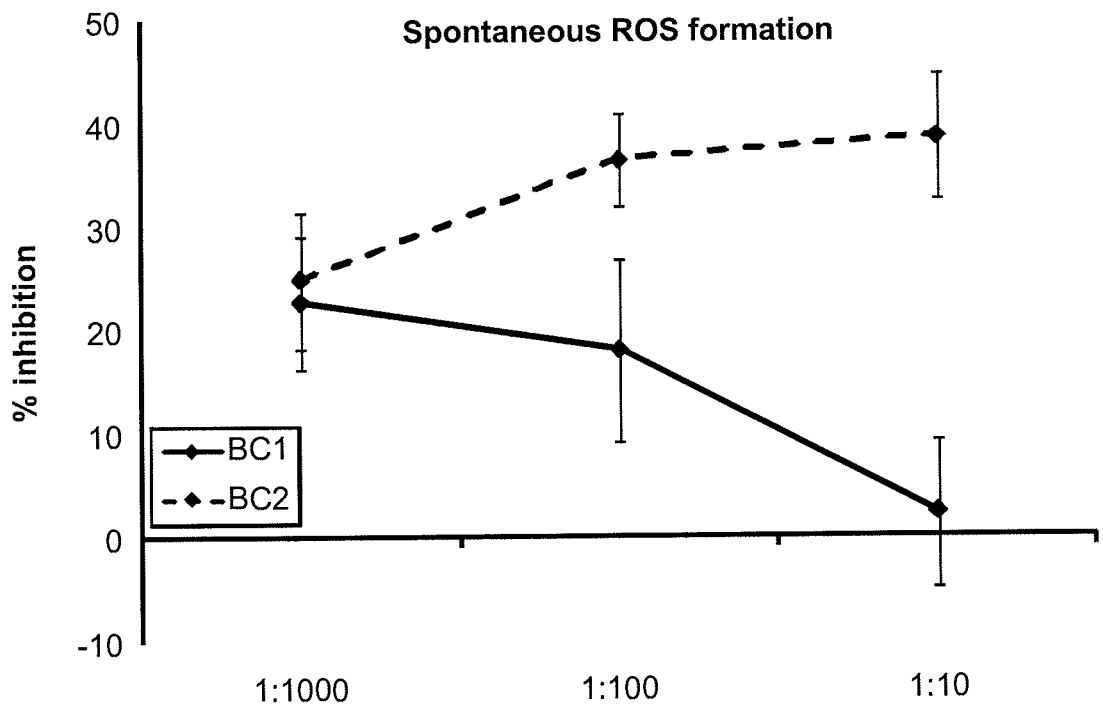
FIG. 1 is a line graph demonstrating the percent inhibition of spontaneous reactive oxygen species (ROS) formation after polymorphonuclear leukocyte (PMN) exposure to either *Bacillus coagulans* supernatant (BC1) or *Bacillus coagulans* cell wall components (BC2), compared to baseline results.

The present invention is directed to the discovery that non-pathogenic lactic acid-producing bacteria (i.e., "lactic acid bacteria"), such as *Bacillus coagulans*, are useful in boosting the immune system, i.e., increasing the level of activation of immune cells. *Bacillus coagulans* vegetative cells and/or spores are used or inactivated/dead *Bacillus coagulans* are used, e.g., heat killed *Bacillus coagulans*. For example, the administration of cell wall components or culture supernatants of *Bacillus coagulans* boosts the immune system by increasing cytokine production, activating the immune surveillance aspect of polymorphonuclear leukocytes (PMN), increasing immune cell chemotaxis, activating natural killer (NK) cells, and increasing monocyte phagocytosis.

Probiotic Lactic Acid-Producing Bacteria

A probiotic lactic acid-producing bacterium suitable for use in the described methods and compositions produces acid and is non-pathogenic. Bacterial species include *Bacillus coagulans*, e.g., *Bacillus coagulans* hammer, preferably *Bacillus coagulans* hammer strain Accession No. ATCC 31284, or one or more strains derived from *Bacillus coagulans* hammer strain Accession No. ATCC 31284 (e.g., ATCC Numbers: GBI-20, ATCC Designation Number PTA-6085; GBI-30 or BC$^{30}$, ATCC Designation Number PTA-6086; and GBI-40, ATCC Designation Number PTA-6087; see U.S. Pat. No. 6,849,256 to Farmer).

Viable *Bacillus coagulans* vegetative cells or spores, *Bacillus coagulans* supernatant, and *Bacillus coagulans* cell wall components are useful in the present invention. Purified and/or isolated *Bacillus coagulans* vegetative cells or spores, *Bacillus coagulans* supernatant or *Bacillus coagulans* cell wall components are particularly useful as a probiotic in the compositions described herein. By "purified" or "substantially purified" is meant *Bacillus coagulans* vegetative cells or spores, *Bacillus coagulans* supernatant, or *Bacillus coagulans* cell well components that are substantially free of contaminating microorganisms or other macromolecules, e.g., polysaccharides, nucleic acids, or proteins. A purified preparation contains at least 75%, 85%, 95% or about 100% of the desired composition and is substantially free of other subcellular components such as cytoplasmic organelles. For example, a bacterial cell wall fraction is at least 75%, 80%, 85%, 90%, 95%, 98%, 99%, or about 100% cell wall components. Such a preparation is sustainably free of cytoplasm intracellular organelles and secreted bacterial products.

The compositions include *Bacillus coagulans* vegetative cells or spores, *Bacillus coagulans* supernatant, or *Bacillus coagulans* cell wall components in the form of a powder, a dried cell mass, a stabilized paste, or a stabilized gel. *Bacillus coagulans* vegetative cells or spores, *Bacillus coagulans* cell wall and/or *Bacillus coagulans* culture supernatant is used in the methods described herein for boosting the immune system. Optionally, the *Bacillus coagulans* cell wall and/or *Bacillus coagulans* culture supernatant is dried and reconstituted in water or other aqueous solution before use.

Because *Bacillus* spores are heat and pressure-resistant and can be stored as a dry powder, they are particularly useful for formulation into and manufacture of products such as the various compositions described herein. A *Bacillus* species is well suited for the present invention, particularly species having the ability to form spores which are relatively resistant to heat and other conditions, making them ideal for storage (shelf-life) in product formulations.

Optionally, the compositions comprise *Bacillus coagulans* vegetative cells and/or spores. The cells/spores are formulated in a variety of compositions suited for use in an immune-boosting composition. In one aspect, the bacterium is present as a mixture of spores and vegetative cells. In another aspect, the bacterium is present as at least 90% spores, e.g., 95%, 98%, or 99% spores. Optionally, prior to addition to the compositions of the invention, the *Bacillus coagulans* cells are cultured in liquid in the absence of or with limited quantities of a food source to induce sporulation. In another aspect, heat gun spray drying kills about 50%, about 75%, about 90%, about 95%, or about 99% of vegetative cells prior to addition to the compositions of the invention. In one aspect, at least about 5%-25% of the bacteria in the composition are viable, e.g., at least about 25%-50%; at least about 50%-75%; or at least about 75%-99% of the bacteria are viable. In another aspect, the composition comprises at least about $1 \times 10^6$ to $1 \times 10^7$; at least about $1 \times 10^7$ to $1 \times 10^8$; or at least about $1 \times 10^8$ to $1 \times 10^9$ viable bacteria.

The invention also provides *Bacillus coagulans* cell wall and/or *Bacillus coagulans* culture supernatant for use in the methods described herein for boosting the immune system. In one aspect, *Bacillus coagulans* bacteria, cell wall components, or culture supernatant in the form of a spray-dried powder is included in or on the surface of the composition described herein. In one aspect, the isolated *Bacillus coagulans* is in the form of a spore. The isolated *Bacillus coagulans* are at least 85%, at least 90%, at least 95%, or at least 99% pure spores. Alternatively, the isolated *Bacillus coagulans* is in the form of a vegetative cell. In one aspect, the isolated *Bacillus coagulans* are at least 85%, at least 90%, or at least 95% pure vegetative cells. In another aspect, the isolated *Bacillus coagulans* is in the form of a mixture of vegetative cells and spores. The *Bacillus coagulans* mixture is 90% spores, 10% vegetative cells; 75% spores, 25% vegetative cells; 60% spores, 40% vegetative cells; 50% spores, 50% vegetative cells; 60% vegetative cells, 40% spores; 75% vegetative cells; 25% spores; or 90% vegetative cells, 10% spores.

The *Bacillus* and/or *Bacillus coagulans* isolated active agent, e.g., *Bacillus coagulans* cell wall and/or *Bacillus coagulans* culture supernatant is applied using any of a variety of known methods including, for example, applying a powder, spray-drying the probiotic onto the composition, or soaking the composition in a solution containing the probiotic. Optionally, the *Bacillus coagulans* cell wall and/or *Bacillus coagulans* culture supernatant is dried and reconstituted in water before use. In another aspect, *Bacillus coagulans* bacteria in the form of spray-dried powder administered directly. Optionally, the composition comprises about $5 \times 10^7$ CFU *Bacillus coagulans* bacteria (per gram of composition) in the form of spray-dried powder.

Any of a variety of methods for placing the bacterial composition into a composition can be used. However, preferred methods include a "spray-dry" method in which the compositions are exposed in a low humidity chamber to an atomized mix containing a liquid composition, where the chamber is subsequently exposed to approximately 80-110° F. to dry the liquid, thereby impregnating the material of composition with the components.

A typical concentration is from approximately $1 \times 10^7$ to $1 \times 10^{12}$ CFU; $1 \times 10^8$ to $1 \times 10^{11}$ CFU; or $1 \times 10^9$ to $1 \times 10^{10}$ CFU of viable bacterium or spores/g of composition. Following drying, the composition is ready for immediate use or for storage in a sterile package.

The active ingredients (i.e., live bacteria, extracellular components, or cell wall components), comprise between about 0.01% to about 10%; 0.01% to about 1%; or about 0.05% to about 0.1% by weight of the composition. Optionally, the isolated *Bacillus coagulans* comprise about 1 mg to about 10 g; about 10 mg to about 1 g; or about 25 mg to about 75 mg by weight of the composition. Most preferably, the amount of *Bacillus coagulans* bacteria is about $5 \times 10^7$ colony forming units (CFU) of bacteria per gram of composition.

In one aspect, the amount of bacteria is about $10^4$ to $10^{14}$ colony forming units (CFU) of bacteria per gram of probiotic composition (i.e., vegetative cells and/or bacterial spores), preferably $10^5$ to $10^{13}$ CFU/g of composition. Alternatively, the concentrations are $10^8$ to $10^{13}$ CFU/g; $10^9$ to $10^{12}$ CFU/g; or $10^{10}$ to $10^{11}$ CFU/g of composition. In one aspect, the amount of bacteria is about $1 \times 10^6$ CFU per gram of composition. The actual amount in a composition will vary depending upon the amounts of composition to be dispersed into the composition and upon routes of dispersal.

In one aspect, the invention provides for storing the composition in a sterile package at room temperature prior to consumption. Alternatively, the composition is used immediately. In another aspect, the composition comprises at least 85%, at least 90%, at least 95% or 100% isolated *Bacillus coagulans* spores.

By way of example, and not of limitation, *Bacillus coagulans* spores may be incorporated into any type of dry or lyophilized product which is dissolved or mixed with hot water, so long as the temperature of the *Bacillus coagulans* mixture is raised to the required heat-shock temperature (i.e., 80° C. for 5 minutes) necessary for germination of the spores. The *Bacillus coagulans* spores may be incorporated into the dry or lyophilized product by the manufacturer.

In one aspect, the *Bacillus coagulans* spores survive storage (shelf-life), i.e., retain viability or the ability to germinate at physiological conditions (e.g., ingestion), from about 12 days to about 2 years; from about 1 month to about 18 months; from about 3 months to about 1 year; or from about 6 months to about 9 months.

Antimicrobial Agents

Optionally, the compositions of the invention also include known antimicrobial agents, known antiviral agents, known antifungal agents. The other agents in the compositions can be either synergists or active agents. Preferably, the known antimicrobial, antiviral and/or antifungal agents are probiotic agents compatible with *Bacillus coagulans*. The compositions may also include known antioxidants, buffering agents, and other agents such as coloring agents, flavorings, vitamins or minerals. Thickening agents may be added to the compositions such as polyvinylpyrrolidone, polyethylene glycol or carboxymethylcellulose.

In one aspect, the active agents are combined with a carrier that is physiologically compatible with the dermal or epithelial tissue of a human or animal to which it is administered. That is, the carrier is preferably substantially inactive except for surfactant properties used in making a suspension of the active ingredients. The compositions may include other physiologically active constituents that do not interfere with the efficacy of the active agents in the composition.

A formulated composition of this invention may be completed in weight using any of a variety of carriers and/or binders. In one aspect, carriers are solid-based dry materials for formulations in tablet, granule or powdered form, and can be liquid or gel-based materials for formulations in liquid or gel forms. Typical carriers for dry formulations include trehalose, malto-dextrin, rice flour, micro-crystalline cellulose (MCC) magnesium stearate, inositol, FOS, gluco-oligosaccharides (GOS), dextrose, sucrose, and the like carriers. Other exemplary composition formulations include a pill, a capsule, or a suspension.

Chemicals used in the present compositions can be obtained from a variety of commercial sources, including Spectrum Quality Products, Inc (Gardena, Calif.), Seltzer Chemicals, Inc., (Carlsbad, Calif.) and Jarchem Industries, Inc., (Newark, N.J.).

As described in detail below, the *Bacillus coagulans* vegetative cells or spores, *Bacillus coagulans* supernatant, and *Bacillus coagulans* cell wall components of the invention are useful in enhancement of the immune response. Enhancement of the immune response comprises an increase in cytokine (e.g., IL-2, IL-4, IL-6, IL-10, TNF-α, or IFN-γ) production or an increase in immune cell migration to an infection site. Immune enhancement also includes boosting the immune system by increasing cytokine production, activating the immune surveillance aspect of polymorphonuclear leukocytes (PMN), increasing immune cell chemotaxis, activating NK cells, and/or increasing monocyte phagocytosis.

EXAMPLE 1

Preparation of *Bacillus coagulans* Cultures

*Bacillus coagulans* Hammer bacteria (ATCC Accession No. 31284) was inoculated and grown to a cell density of about $10^8$ to $10^9$ cells/ml in nutrient broth containing 5 g Peptone, 3 g Meat extract, 10-30 mg $MnSO_4$, and 1,000 ml distilled water, adjusted to pH 7.0, using a standard airlift fermentation vessel at 30° C. The range of $MnSO_4$ acceptable for sporulation is 1 mg/l to The vegetative cells can actively reproduce up to 45° C., and the spores are stable up to 90° C. After fermentation, the *B. coagulans* bacterial cells or spores are collected using standard methods (e.g., filtration, centrifugation) and the collected cells and spores can be lyophilized, spray-dried, air-dried or frozen. As described herein, the supernatant from the cell culture is collected and used as source of extracellular agents secreted by *B. coagulans*.

A typical yield from the above culture is in the range of about $10^9$ to $10^{10}$ viable spores and more typically about 100 to 150 billion cells/spores per gram before drying. Spores maintain at least 90% viability after drying when stored at room temperature for up to ten years, and thus the effective shelf life of a composition containing *B. coagulans* Hammer spores at room temperature is about 10 years.

EXAMPLE 2

Preparation of *Bacillus coagulans* Spores

A culture of dried *B. coagulans* spores was prepared as follows. Ten million spores were inoculated into a one liter culture containing 24 g potato dextrose broth, 10 g of enzymic-digest of poultry and fish tissue, 5 g of FOS and 10 g $MnSO_4$. The culture was maintained for 72 hours under a high oxygen environment at 37° C. to produce culture having about 150 billion cells per gram of culture. Thereafter, the culture was filtered to remove culture medium liquid, and the bacterial pellet was re-suspended in water and freeze-dried. The freeze-dried powder is then ground to a fine powder using standard good manufacturing practice (GMP).

EXAMPLE 3

Immunomodulatory and Anti-Inflammatory Effects of $BC^{30}$ In Vitro

*Bacillus coagulans* (BC) is a gram-positive rod that forms heat-resistant and acid-resistant spores. Oral consumption of spores or encapsulated spores allows transient colonization of the intestines with BC cultures. The spores germinate and the bacterial cultures grow and ferment the food in the intestinal lumen.

Immune activation was induced in cultures of human immune cells when exposed to a) purified *Bacillus coagulans* culture supernatant (BC1), or b) purified *Bacillus coagulans* cell wall components (BC2). These two fractions were utilized to characterize the interactions between *Bacillus coagulans* and immune cells in vivo, e.g., the Lamina Propria or Peyer's Patches located in the lumen of the intestines. *Bacillus coagulans* supernatant (BC1) and *Bacillus coagulans* cell wall components (BC2) were tested in parallel using a panel of cell-based assays in vitro.

*Bacillus coagulans* was found to positively affect immune cells in the gut: 1) secreted bacterial factors were found to affect/modulate immune cell function; and 2) interaction of bacterial cell wall components with Toll-like and/or other immune cell surface receptors led to modulation of immune cell function. BC cell walls contain unique components that interact with immune cells in such a way as to activate or boost the immune system. BC also secretes metabolites and/or other factors that are produced when BC is growing in the environment of the small intestine. Such metabolites/factors include, but are not limited to antioxidant and anti-inflammatory compounds.

Bacterial Cell Fractionation

A sample of *Bacillus coagulans* spores was heat-activated at 50° C. and inoculated in liquid medium. The sample was incubated at 37° C. for 24 hours. This time period allows the formation of a log-phase bacterial culture where death and bacterial breakdown is not prominent. After the incubation, the two fractions (*Bacillus coagulans* supernatant (BC1) and *Bacillus coagulans* cell wall components (BC2)) were prepared. The initial separation occurred by decanting the entire culture into a 50 mL vial followed by centrifugation at 2400 rpm. This resulted in the bacteria forming a pellet. The supernatant was gently decanted into a new vial. From this vial, smaller 1 mL samples were aliquoted into Eppendorf vials and subjected to high speed centrifugation, followed by two serial filtrations with a 0.2 um filter, to eliminate any intact bacteria and fractions thereof. The sterile, filtered supernatant was aliquoted and multiple aliquots frozen and stored at −20° C. For later biological assays, one aliquot was thawed on each testing day.

The original pellet from the initial centrifugation was used to prepare the cell wall fraction. The wet pellet was frozen and thawed several times to break open the bacterial walls so that the intracellular compounds could be removed by washing. The thawed slush was transferred to an Eppendorf vial and washed twice in physiological saline using high speed centrifugation. Then the pellet was transferred to a glass vial and subjected to bead milling using low-protein-binding Zirconium beads with a diameter of 200 micrometer. The milling was performed by repeated 'pulsing' using a Vortex mixer. This method is effective to break up cell walls. The beads were removed and the slush containing the broken cell wall fragments were sterile-filtered into multiple aliquots that were frozen immediately and stored at −20° C. For later assays, one aliquot was thawed on each testing day.

Purification of Peripheral Blood Mononuclear Cells and Polymorphonuclear Cells

Healthy human volunteers between the ages of 20 and 50 years served as blood donors upon informed consent, as approved by the Sky Lakes Medical Center Institutional Review Board (FWA 2603). Freshly drawn peripheral venous blood samples in sodium heparin were layered onto a double-gradient of Histopaque 1119 and 1077, and centrifuged for 25 minutes at 2400 revolutions per minute (rpm). The upper, peripheral blood mononuclear cells (PBMC)-rich and lower polymorphonuclear (PMN) interfaces were harvested using sterile transfer pipettes into new vials, and washed twice with 10 mL phosphate buffered saline (PBS) without calcium or magnesium by centrifugation at 2400 rpm for 10 minutes.

Phagocytosis Assay

Evaluation of phagocytic activity was performed using human PMN cells. The choice of particles for phagocytosis was carboxylated Fluorospheres (Molecular Probes, Eugene Oreg.). An aliquot of 0.05 mL Fluorobeads was removed from the stock bottle into a 1.5 mL microcentrifuge tube and washed twice in PBS. Fluorobeads were then re-suspended in 7.5 mL RPMI 1640. PMN cells were plated into 96-well plates in RPMI-1640 at a concentration of $2 \times 10^6$ cells/mL. Ten microliters of 10-fold serial dilutions of BC1 or BC2 were added to test wells in quadruplicate, and PBS was added to control wells in quadruplicate. The plate was immediately centrifuged, and the supernatant removed. The cells were re-suspended in RPMI-1640 containing Fluorobeads, and then incubated for 2 minutes with Fluorospheres with continuous pipetting. The phagocytic activity was stopped by adding PBS with 0.02% sodium azide. Cells were washed twice in PBS with sodium azide to remove beads not ingested by the cells. Samples were transferred into vials for flow cytometry, ensuring the continued presence of sodium azide. Samples were acquired by flow cytometry immediately (FacsCalibur, Becton-Dickinson San Jose, Calif.). The analysis was performed using the FlowJo software (TreeStar Inc., Ashland Oreg.). During analysis, electronic gating for the PMN population was performed using the forward and side scatter properties. The relative amount of phagocytosis within the PMN population in each sample was evaluated by the mean fluorescence intensity (MFI) for the green fluorescence. The MFI (green) for the untreated samples showed the relative amount of phagocytosis in the absence of BC1 and BC2. The MFI (green) for the BC1 and BC2 treated samples were compared to untreated samples.

Reactive Oxygen Species (ROS) Production by PMN cells

Parallel samples of PMN cells were incubated at 37° C., 5% $CO_2$ for 20 minutes, either untreated or with test products over a range of 10-fold serial dilutions (1:10, 1:100, 1:1000). The precursor dye dichlorofluorescin diacetate (DCF-DA), which becomes brightly green fluorescent upon exposure to free radicals, was prepared by adding 0.18 mL DMSO to a 0.05 mg aliquot of DCF-DA. A working solution of DCF-DA was then prepared by adding 0.01 mL stock to 10 mL PBS. The PMN cells were washed three times in PBS and then re-suspended in the DCF-DA working solution and incubated for 1 hour at 37° C. All samples, except for the untreated control samples, were then exposed to 167 mM $H_2O_2$ for a period of 45 minutes to induce ROS production. Samples were washed twice in PBS to remove the peroxide, and transferred to vials for flow cytometry. The DCF-DA fluorescence intensity in untreated versus $H_2O_2$-challenged cells was analyzed by flow cytometry. Data was collected in quadruplicate for controls, and duplicate for each dose of BC1 and BC2. The relative amount of ROS formation in PMN cells was evaluated by green fluorescence intensity.

PMN Cell Random Migration and Chemotactic Migration Towards Three Chemo-Attractants: f-MLP, IL-8 and Leukotriene B4

Figure 3:
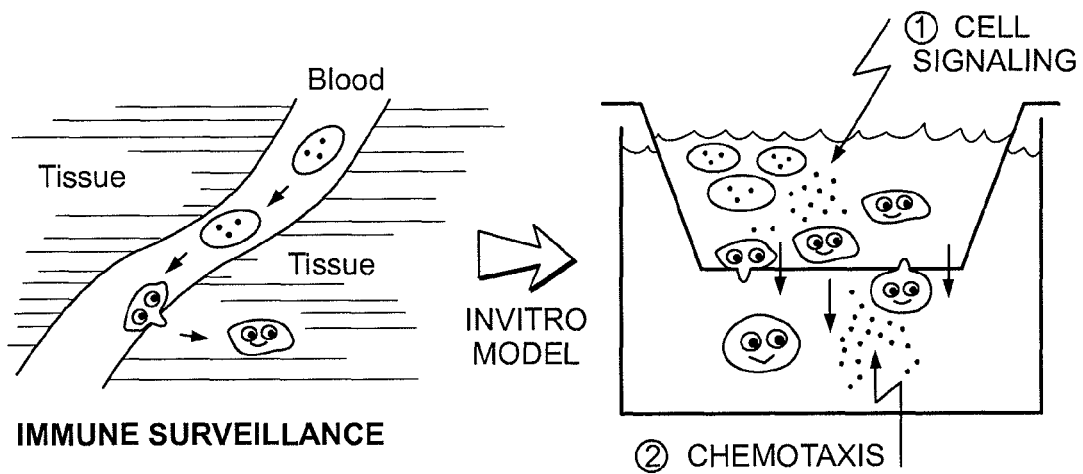
FIG. 3 is a schematic representation of how PMN migration begins in the blood stream and moves into the tissue via transwell migration plates.

The PMN cell is a highly active and migratory cell type (FIG. 3). The differential effect on PMN cell migration towards the bacterial peptide formyl-Met-Leu-Phe (f-MLP) and two different inflammatory chemo-attractants IL-8 and Leukotriene B4 (LTB4) was tested. The following experimental model was performed in quadruplicate in order to obtain data significance. Cells were incubated with 10-fold serial dilutions of GBI-30 (GanedenBC$^{30}$™) supernatant or cell wall fractions for 10 minutes in a polystyrene round-bottom tube before plating commenced. During this time the Millipore trans-well (3.0 μm pore size) migration plate was coated with 50 μg/mL Fibronectin for a period of 30 minutes. Chemoattractants and RPMI 1640 were then added to the appropriate bottom chamber wells of the trans-well migration plate in a volume of 150 μL: f-MLP (10 nM), Interleukin-8 (10 μg/mL), and Leukotriene B4 (10 nM). Fibronectin was removed from the top wells by aspiration before plating of cells. Fifty microliters of cells ($1×10^6$/mL) were plated in the top chambers, and the top chamber plate was then lowered into the bottom plate and allowed to incubate overnight at 37° C. Quantification of the relative amount of migrated cells was performed by fluorescent CyQuant® staining of the cells that had accumulated in the bottom chambers. Fluorescence intensity was quantified in a Tecan Spectrafluor fluorescence plate reader.

Externalization of CD 107a on NK Cells in Response to K562 Tumor Cells

Freshly purified human peripheral blood mononuclear cells (PBMC) re-suspended in RPMI 1640 were used for this assay. The cells were plated at $2×10^5$/well in round-bottom 96-well micro-assay plates, and treated with serial dilutions of the test products in triplicate. Negative control wells in triplicate were left untreated. In addition, 3 wells containing PBMC alone and K562 cells alone served as negative controls for baseline CD107a expression. $1×10^6$ K562 cells, an NK-cell sensitive tumor cell line widely used in NK cell cytotoxicity studies, were added to wells containing PBMC with product and untreated PBMC. The two cell types were loosely pelleted by a brief 30-second centrifugation at 2400 rpm followed by incubation at 37° C. for 45 minutes. Cells were transferred to V-bottom microtiter plates for processing and staining. Cells were stained with CD3-PerCP, CD56-PE and CD107a-FITC. The expression of CD107a on the NK cells was determined by flow cytometry. The CD3 negative, CD56 positive NK cells were differentiated from the K562 cells based on forward and side scatter properties, and from other lymphocytes by electronic gating on $CD3^-$, $CD56^+$ cells, followed by evaluation of fluorescence intensity for CD 107a.

Induction of Natural Killer Cell Activation Markers and Immuno-Staining

Freshly isolated PBMC were plated in a sterile U-bottom 96-well culture plates (NUNC, Denmark) and treated with serial dilutions of test products. For activation of natural killer (NK) and natural killer T (NKT) cells the incubation time was 18 hours. Cells were transferred to V-bottom 96-well plates (NUNC Denmark) and washed in IF buffer (PBS containing 1% bovine serum albumin and 0.02% sodium azide). Cells were re-suspended in 0.05 mL IF buffer and monoclonal antibodies were added in previously established optimal quantities (CD3-PerCP, CD56-PE, CD69-FITC, and CD25-FITC: 8 μL/sample), and incubated in the dark at room temperature for 10 minutes. The cells were washed twice with an additional 0.15 mL of PBS with 0.02% azide. Following centrifugation and aspiration of the supernatant, the cells were re-suspended in 0.05 mL PBS with 0.02% azide and transferred to 5 mL polystyrene round-bottom tubes each containing 0.4 mL of 1% formalin. Samples were stored in the dark and acquired by flow cytometry within 24 hours using a FACSCalibur flow cytometer (Becton-Dickinson, San Jose Calif.). Analysis was performed using the FlowJo (Tree Star Inc., Ashland Oreg.) software.

Modulation of Proliferation and Cytokine Production in Response to PHA and PWM

Freshly purified PBMC re-suspended in RPMI 1640 supplemented with 10% fetal calf serum, L-glutamine (5 mM), penicillin (100 U/mL) and streptomycin (100 mg/mL) were plated in a U-bottom cell culture plate at a volume of 180 μL at a concentration of $1×10^6$/mL. Next, 20 μL of 10-fold serial dilutions of BC1 and BC2 were added to the individual wells in triplicate. In a parallel set of wells, the combinatorial effect of BC1 and BC2 with known mitogens was tested. Mitogens were added at a concentration of 5 μL of PWM (200 μg/mL) and 4 μL of PHA (2 μg/mL) to initiate proliferation. The plate was sealed with parafilm and was incubated at 37° C., 5% $CO_2$ for 5 days. After 5 days the cells were transferred to a flat-bottom black 96-well plate and the relative cell numbers in each culture well quantified by CyQuant® staining and a Tecan Spectrafluor fluorescence plate reader.

Cytokine Bead Array

Supernatants from the 5-day lymphocyte proliferation cultures were harvested and relative levels of the 6 cytokines: IL-2, IL-4, IL-6, IL-10, TNF-α, and IFN-γ were measured using a flow cytometry-based bead array kit (CBA human Th1/Th2 cytokine kit II, BD Biosciences, San Jose, Calif.). Samples were tested in duplicate according to the manufacturer's specifications, and data acquired immediately by flow cytometry, using a FacsCalibur flow cytometer (Becton-Dickinson San Jose, Calif.). The analysis was performed using the FlowJo software (TreeStar Inc., Ashland, Oreg.).

Statistical Analysis

Statistical analysis involved simple comparisons between two mean values, and was performed using Microsoft Excel. Statistical significance was tested using Student's t-test with a p value of less than 0.05 indicating a statistically significant difference between two data sets.

Anti-Bacterial Defense Mechanisms

As described in detail below, *Bacillus coagulans* supernatant induced phagocytosis at the highest dose tested, in both PMN (polymorphonuclear—white blood cell (WBC)) cells and monocytes (FIGS. 34-35). Both *Bacillus coagulans* supernatant (BC1) and *Bacillus coagulans* cell wall components (BC2) induced random PMN cell migration, i.e., their scavenging activity for invading bacteria (part of normal immune surveillance). Both fractions, but especially the supernatant, induced PMN cell migration towards a bacterial peptide f-MLP, indicating that *Bacillus coagulans* GanedenBC30™ enhanced the PMN "attack" when a bacterial invasion was mimicked. Both fractions, but especially the supernatant, also enhanced the PMN migration when the *Bacillus coagulans* GanedenBC30™ fractions were mixed together with f-MLP, i.e., to simulate an in vivo situation in which *Bacillus coagulans* GanedenBC30™ co-exists with potentially pathogenic bacteria in the gut lumen.

Anti-Viral and Anti-Cancer Defense Mechanisms

NK cells are important in the defense against cancer cells and viruses. Both *Bacillus coagulans* supernatant (BC1) and *Bacillus coagulans* cell wall components (BC2) activated Natural Killer (NK) cells. Both fractions enhanced the aggressive secretion of killer substances from NK cells when the NK cells subsequently were contacted with tumor cells.

Anti-Inflammatory Effects

*Bacillus coagulans* supernatant (BC1) and *Bacillus coagulans* cell wall components (BC2) have anti-inflammatory effects. *Bacillus coagulans* GBI-30 (GanedenBC30™) fractions were introduced to PMN cells at very low doses. The PMN cells were then coached to migrate towards an inflammatory mediator, Leukotriene B4. This assay mimics the PMN cell's role in maintaining an inflammatory cascade. Ganeden BC30™ supports or inhibits the migration of the inflammatory PMN cells, depending on whether the PMN cell is engaged in normal immune surveillance or is engaged in an inflammatory response.

EXAMPLE 4

Effect of *Bacillus coagulans* on Activation of Phagocytes

For each of the figures described in Example 4, the dilutions on the X-axis refers to the tested dilution of each *Bacillus coagulans* (BC) fraction. For example, a 1:100 dilution is 100-fold dilution of the initial frozen stock solution.

Reactive Oxygen Species (ROS) Production

Many natural products reduce the reactive oxygen species (ROS) formation in inflammatory cells. However, other products increase ROS formation, indicating an inducement of antimicrobial defense mechanisms. Human polymorph nucleated cells (PMN) were used for testing ROS production. This cell type constitutes approximately 70% of the white blood cells in humans. PMN produce high amounts of ROS upon certain inflammatory stimuli.

Freshly purified PMN were exposed to serial dilutions of the two test products, *Bacillus coagulans* supernatant (BC1) and *Bacillus coagulans* cell wall components (BC2) in parallel. During the incubation with test products, any antioxidant compounds able to cross the cell membrane can enter the interior of the PMN cells. The cells were washed and loaded with the DCF-DA dye, which fluoresces upon exposure to reactive oxygen species. Oxidation was triggered by addition of $H_2O_2$. The fluorescence intensity of the PMN cells was evaluated by flow cytometry. The low fluorescence intensity of untreated control cells served as a baseline, while PMN cells treated with $H_2O_2$ alone served as a positive control.

If the fluorescence intensity of PMN cells exposed to *Bacillus coagulans*, and subsequently exposed to $H_2O_2$ is reduced compared to exposure to $H_2O_2$ alone, the test product has anti-inflammatory effects. By contrast, if the fluorescence intensity of PMN cells exposed to a test product is increased compared to $H_2O_2$ alone, a test product has pro-inflammatory effects.

As shown in FIG. 1, the PMN cell is capable of signaling by both anti- and pro-inflammatory mechanisms, which can lead to either enhancement or reduction of the production of reactive oxygen species (ROS). Both BC1 and BC2 showed a clear inhibition of the spontaneous formation of reactive oxygen species in PMN cells. The effect of BC2 showed a dose-dependent inhibition of ROS formation, whereas the effect of BC1 showed stronger anti-inflammatory effect at the lowest doses tested. BC1 and BC2 presented roughly a 25% inhibition of baseline ROS formation at the highest dilution of 1:1000. The presence of BC1 (1:1000) reduced spontaneous ROS formation by 22% (P<0.003). BC2 (1:1000) showed a similar effect on lowering ROS formation (P<0.004). However, at the 1:10 dilution of BC2 this effect was even stronger, resulting in a 38% reduction in spontaneous ROS formation (P<0.0002). The inhibition was highly significant (P<0.01) for all dilutions of BC2, and for the 1:1000 dilution of BC1. The 1:100 dilution of BC1 was close to being highly significant (P=0.0137).

Figure 2:
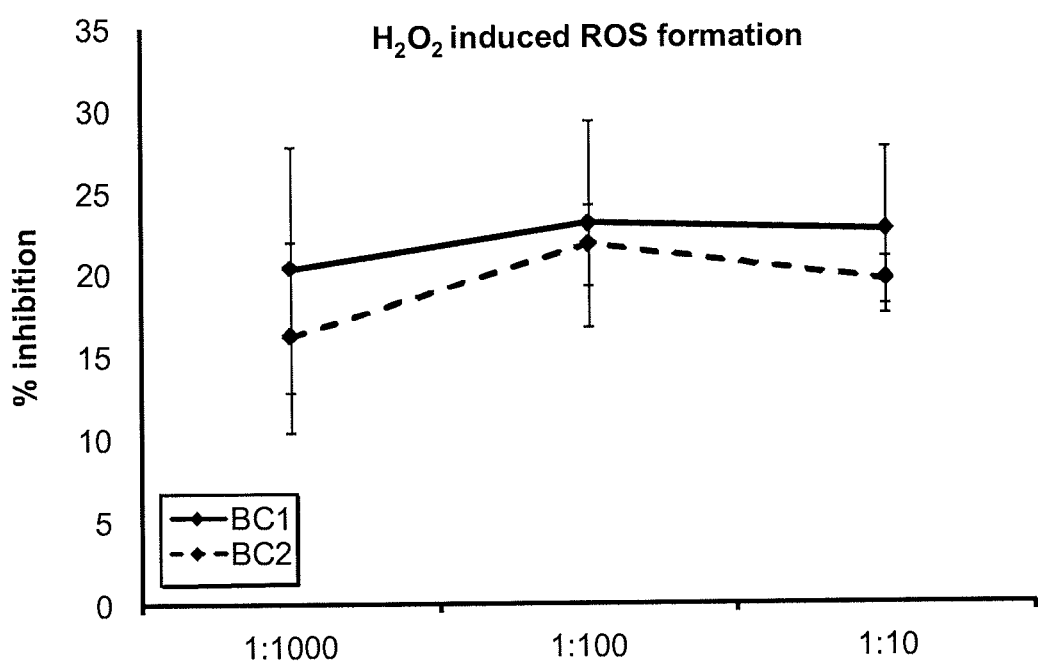
FIG. 2 is a line graph illustrating the percent inhibition of $H_2O_2$-induced ROS formation compared to baseline results.

As shown in FIG. 2, when cells were treated with BC1 and BC2 and then exposed to oxidative stress ($H_2O_2$), the cells showed a reduced production of ROS compared to the negative control. Inhibition remained at a constant rate of 16-23%. These inhibitions were statistically significant (P<0.05) for both fractions at all dilutions except BC2 at 1:1000 (P=0.0539). Both fractions showed highly significant inhibition of ROS production at the 1:1000 dilution. BC1 (1:100) reduced ROS formation by 23% (P<0.02) while BC2 (1:100) reduced ROS formation by 21% (P<0.008).

Differential Effect on PMN Cell Random Migration and Chemotactic Migration Towards Three Chemo-Attractants: f-MLP, IL-8, and Leukotriene B4 (LTB-4)

The PMN cell is a highly active and migratory cell type that plays a major role in immune surveillance. The migratory behavior of PMN is divided into at least two types: a) random migration and b) directed migration. Random migration is part of normal immune surveillance, while directed migration is migration toward specific chemoattractants.

Both random migration and directed migration were tested in parallel. Directed migration toward the following three distinctly different chemotactic compounds was examined: i)

bacterial peptide f-Met-Leu-Phe (fMLP); ii) the inflammatory cytokine Interleukin-8 (IL-8); and iii) Leukotriene B4 (LTB4).

Some test products may specifically reduce directed PMN migration towards the inflammatory mediators IL-8 and/or LTB4, while allowing PMN migration toward bacterial peptides as part of the normal anti-bacterial immune defense. The testing of migration towards several inflammatory chemoattractants helps identify selective responses in this in vitro system, which closely mimics the rat paw edema in vivo model of inflammation. The assay allows for the differentiation between antibacterial immune defense mechanisms and inflammation response mechanisms.

Freshly purified PMN cells were cultured in double-chamber migration plates, the bottom chamber mimicking tissue, and the top chamber mimicking the blood stream (FIG. 3). Cells were plated in the top chambers with or without test products, while different chemoattractants were placed in the bottom chambers. For control wells, cells were placed in the top chamber without a test product and chemo-attractant was not placed in the bottom wells. In this manner, evaluation of baseline random migration was determined. All assays were performed in triplicate, and repeated at least 3 times with consistent results using freshly isolated cells from three different healthy human donors.

Figure 4:
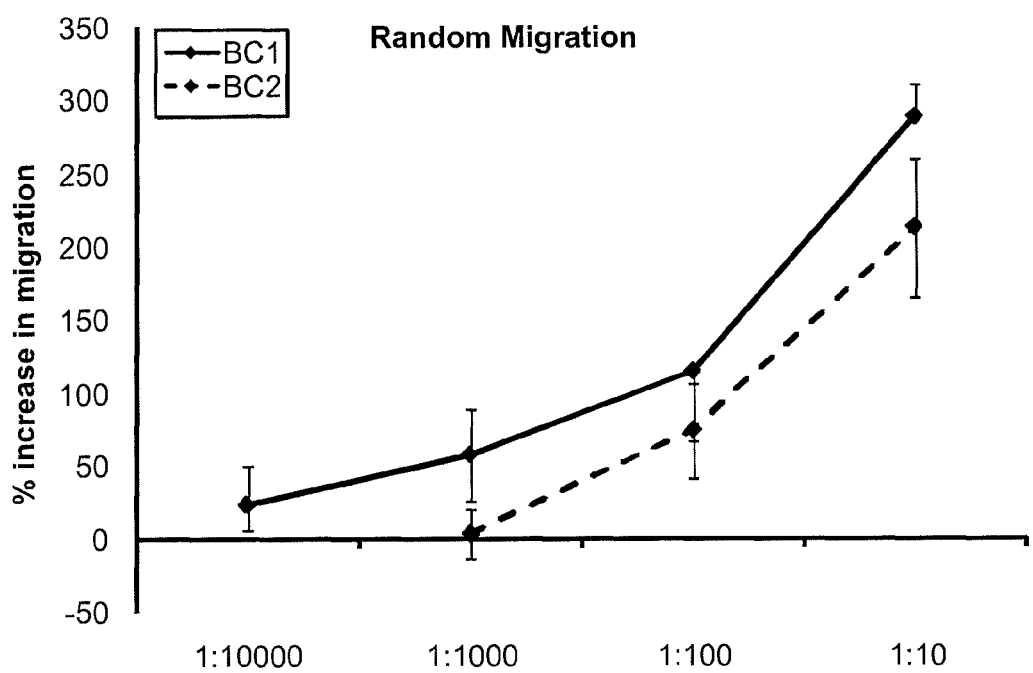
FIG. 4 is a line graph demonstrating random migration showing the migratory patterns of PMN's treated with either *Bacillus coagulans* supernatant (BC1) or *Bacillus coagulans* cell wall components (BC2).
Figure 5:
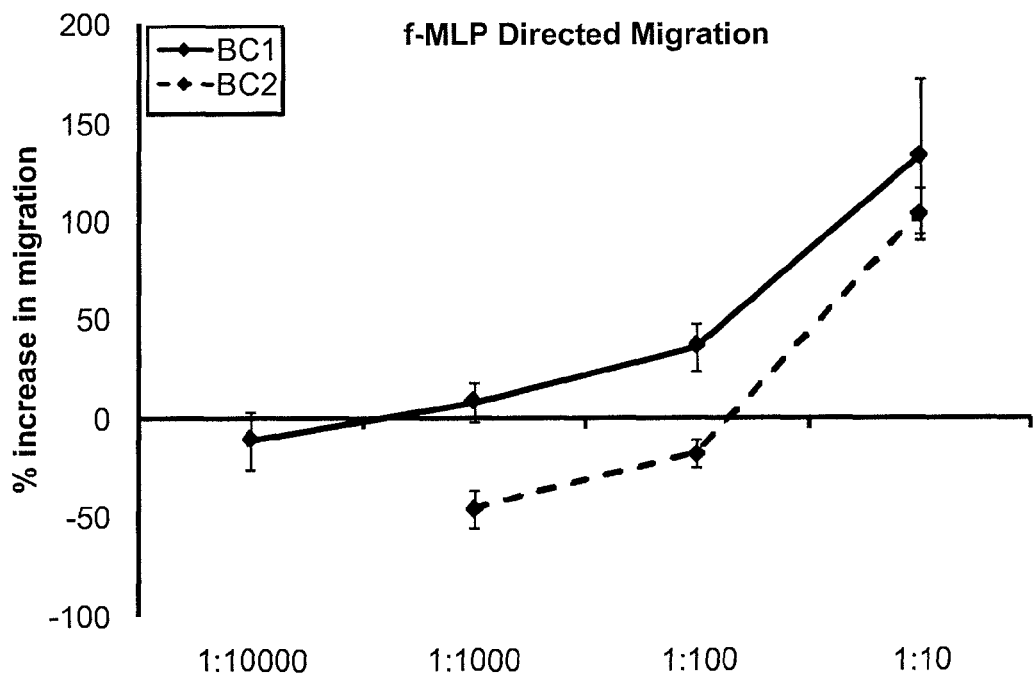
FIG. 5 is a line graph illustrating bacterial peptide formyl-Met-Leu-Phe (f-MLP)-directed migration showing the migratory patterns of PMS's treated with either *Bacillus coagulans* supernatant (BC1) or *Bacillus coagulans* cell wall components (BC2).

*Bacillus coagulans* supernatant (BC1) was tested at one extra dilution, compared to *Bacillus coagulans* cell wall components (BC2). Both fractions of the GanedenBC$^{30}$™ (*Bacillus coagulans*) induced the random migration of PMN cells, indicating that both *Bacillus coagulans* supernatant (BC1) and *Bacillus coagulans* cell wall components (BC2) activated the immune surveillance aspect of PMN cells (FIG. 4). BC1 (1:10) increased the random migration by 300% (p<0.001), and BC2 (1:10) increased the random migration by 200% (p<0.005). Higher doses of both BC1 and BC2 increased the migration towards the bacterial peptide f-MLP, indicating that *Bacillus coagulans* supernatant (BC1) and *Bacillus coagulans* cell wall components (BC2) induced anti-bacterial defense mechanisms (FIG. 5).

Surprisingly, at more dilute concentrations, BC1 and BC2 decreased the amount of f-MLP directed migration, indicating that different levels of *Bacillus coagulans* have different effects on immune cells in the gut. BC1 (1:10,000) decreased f-MLP directed migration by 11%; however, this was not statistically significant, and BC (1:1000) decreased f-MLP directed migration by 46% (P<0.005).

Figure 6A:
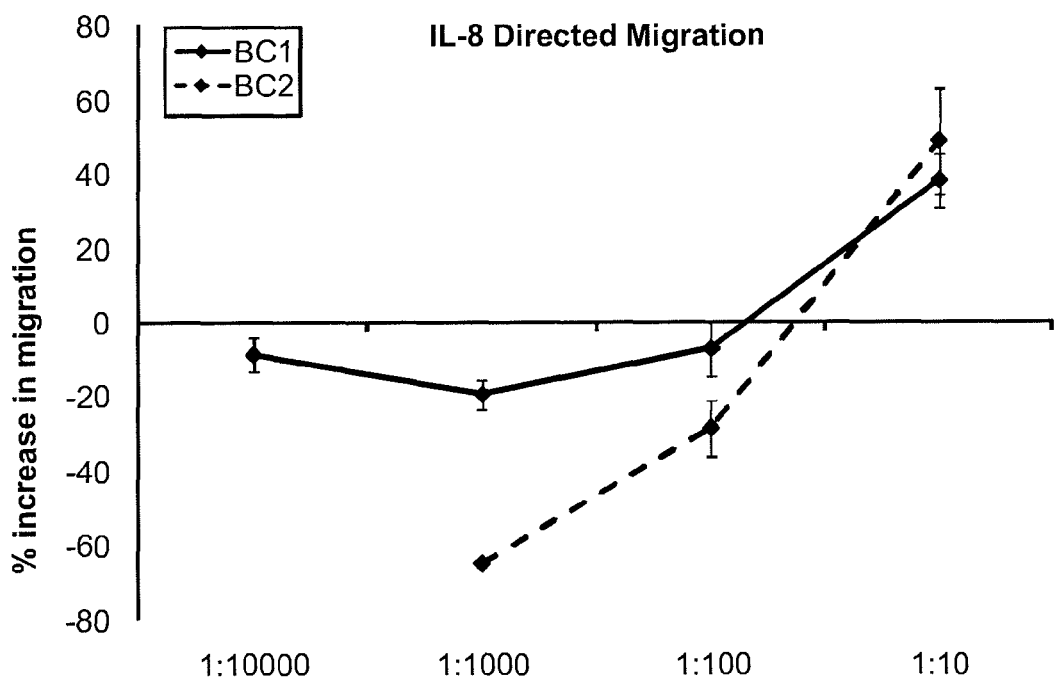
FIG. 6A is a line graph demonstrating interleukin-8 (IL-8)-directed migration showing the migratory patterns of PMN's treated with either *Bacillus coagulans* supernatant (BC1) or *Bacillus coagulans* cell wall components (BC2).

Treatment of PMN cells with higher doses of BC1 and BC2 enhanced IL-8 directed migration (FIG. 6A). This increased migration was highly significant at the 1:10 dilution for both BC1 (P<0.002) and BC2 (P<0.002). By contrast, lower doses of BC1 and BC2 reduced the IL-8 directed migration. At the 1:1000 dilution of BC2, a 65% decrease in migration was seen that was highly statistically significant (P<0.00001).

Figure 6B:
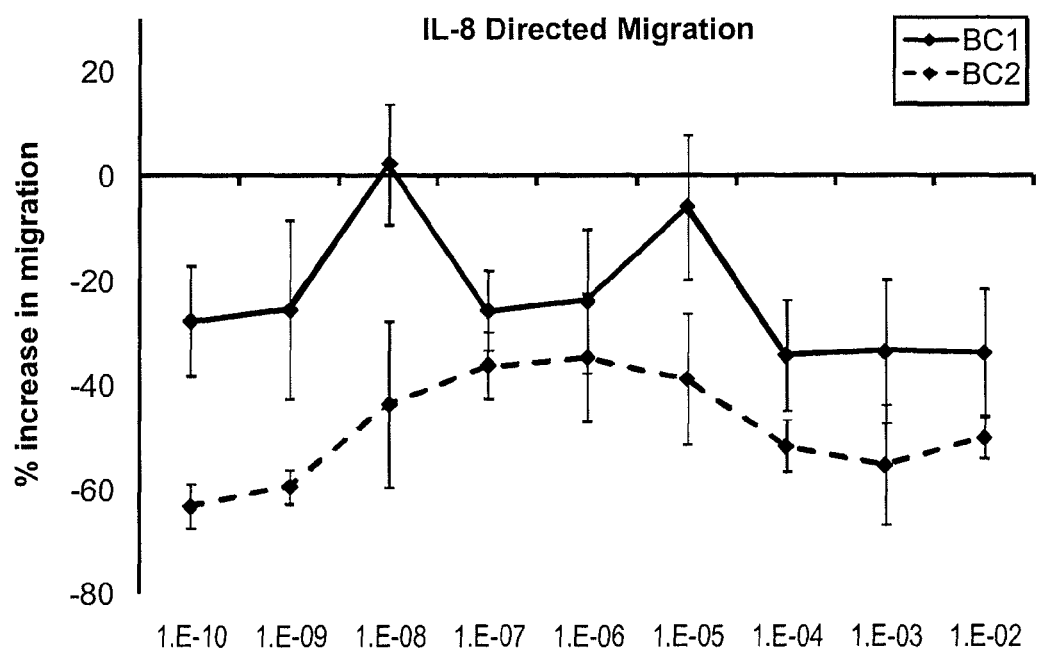
FIG. 6B is a line graph depicting IL-8 directed migration of *Bacillus coagulans* supernatant (BC1) and *Bacillus coagulans* cell wall components (BC2)-treated PMN cells.

A dose study of IL-8 directed PMN migration with much lower doses of both BC1 and BC2 was performed. As shown in FIG. 6B, a reduction of in IL-8 directed PMN migration was demonstrated at all dilutions of BC2. This effect of BC2 was strongest at the $10^{10}$ dilution, where migration was inhibited by 63% (p<0.02). BC1 treatment of PMN cells at low doses also reduced IL-8 directed migration. An interesting pattern of IL-8 directed PMN migration inhibition was seen with both BC1 and BC2. Neither product demonstrated a linear dose curve but rather intermediate doses ($10^4$ to $10^8$) of both BC1 and BC2 showed less inhibition of IL-8 directed migration compared to higher or lower doses. These results indicate that pro- and anti-inflammatory compounds likely co-exist in both *Bacillus coagulans* supernatant (BC1) and *Bacillus coagulans* cell wall components (BC2).

Figure 7A:
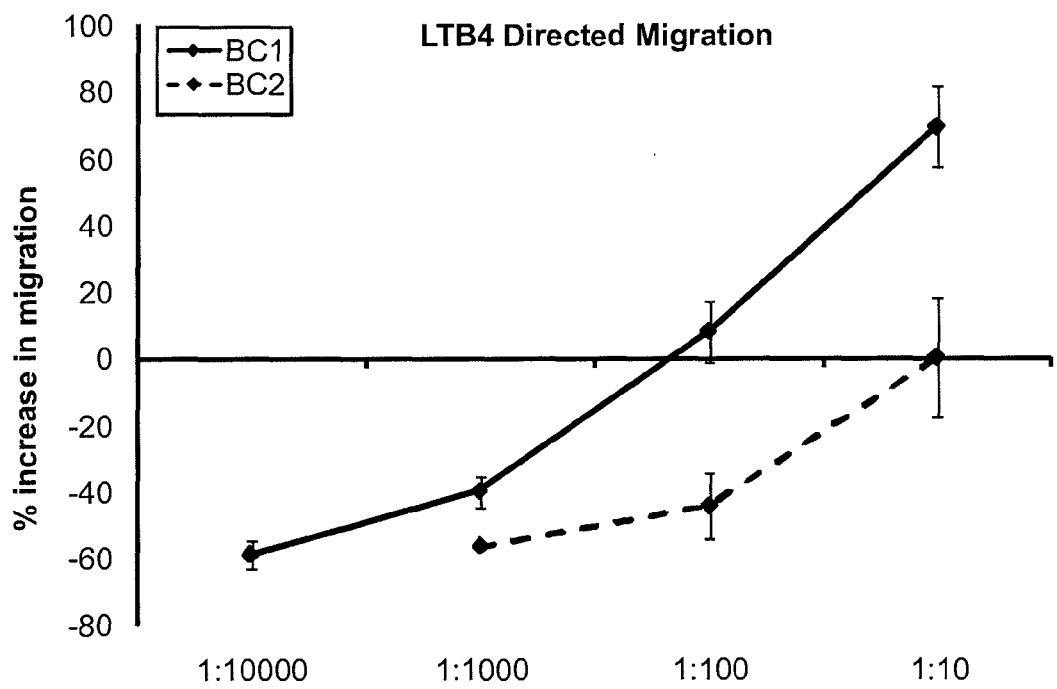
FIG. 7A is a line graph illustrating leukotriene B4 (LTB4)-directed migration showing the migratory patterns of PMN's treated with either *Bacillus coagulans* supernatant (BC1) or *Bacillus coagulans* cell wall components (BC2).
Figure 7B:
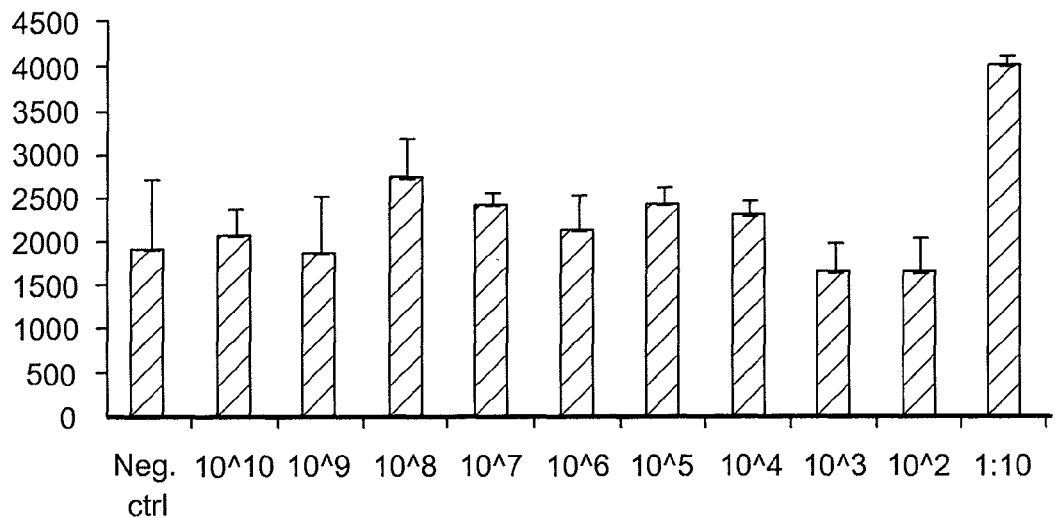
FIGS. 7B-7C are a series of bar charts illustrating LTB4-directed migration.
Figure 7C:
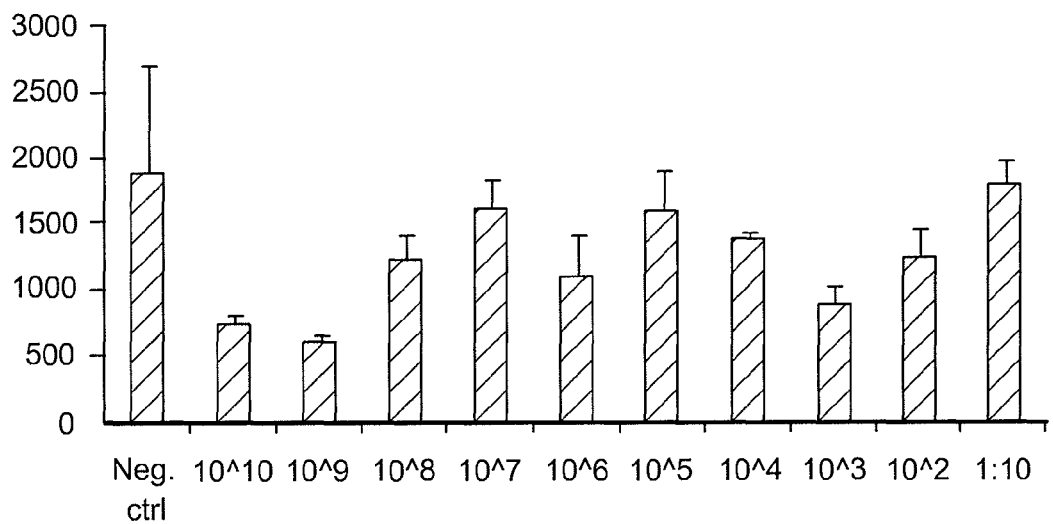

Both BC1 and BC2 fractions also had a dual effect on LTB4 directed PMN migration. At lower doses, both BC1 and BC2 demonstrated a dose-dependent reduction in PMN migration towards LTB4 (FIG. 7). The 1:1000 dilution of BC2 inhibited migration by 52% (p<0.002). Cells treated with 1:1000 (p<0.008) and 1:10000 (p<0.002) dilutions of BC1 also showed anti-inflammatory effect that were highly statistically significant. Conversely, the 1:10 dilution of BC1 resulted in a significant increase in PMN migration towards LTB4 (p<0.003).

Chemoattractant Effect on PMN Cell Migration

Figure 8:
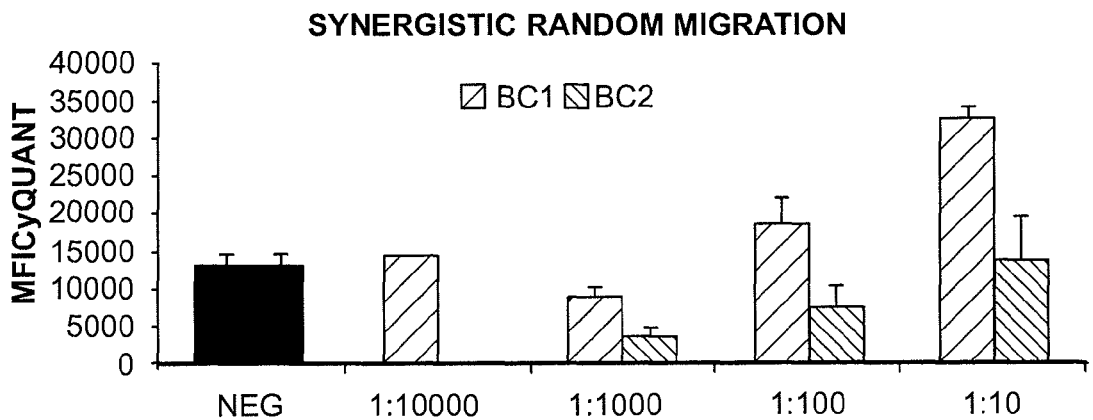
FIG. 8 is a bar graph demonstrating synergistic random migration showing the migratory patterns of PMN's exposed to either *Bacillus coagulans* supernatant (BC1) or *Bacillus coagulans* cell wall components (BC2) acting as a chemoattractant in the bottom chamber of the trans-well migration plate.

The synergistic effect of the following three chemoattractants was examined: bacterial f-MLP, IL-8, and Leukotriene B4 (FIG. 8). This assay tests the migratory properties of PMN cells, using the same set-up as described above; however, the BC fractions were not applied to the top chamber with the cells, but were plated in the bottom chamber, thereby providing a chemotactic gradient. If the test products contained chemoattractant compounds, then the PMN cell migration from the top to the bottom chamber was increased compared to untreated wells.

In one group, the BC fractions were added to the bottom chambers and direct chemoattractant properties of the BC fractions were measured. In another group, the BC fractions were placed in the bottom chambers in combination with each of the following chemoattractants: bacterial f-MLP, IL-8 and Leukotriene B4 in order to examine the synergistic affects on PMN migration in the presence of both the BC fractions and a known chemoattractant.

The two *Bacillus coagulans* fractions have varying effects despite coming from the same bacterial cultures (FIG. 8). Higher doses of *Bacillus coagulans* supernatant (BC1) had a strong chemotactic effect, while *Bacillus coagulans* cell wall components (BC2) did not show any chemoattractant effect, even at the highest dose. By contrast, BC1 decreased the amount of migration, indicating that BC1 has an anti-inflammatory effect.

Figure 9:
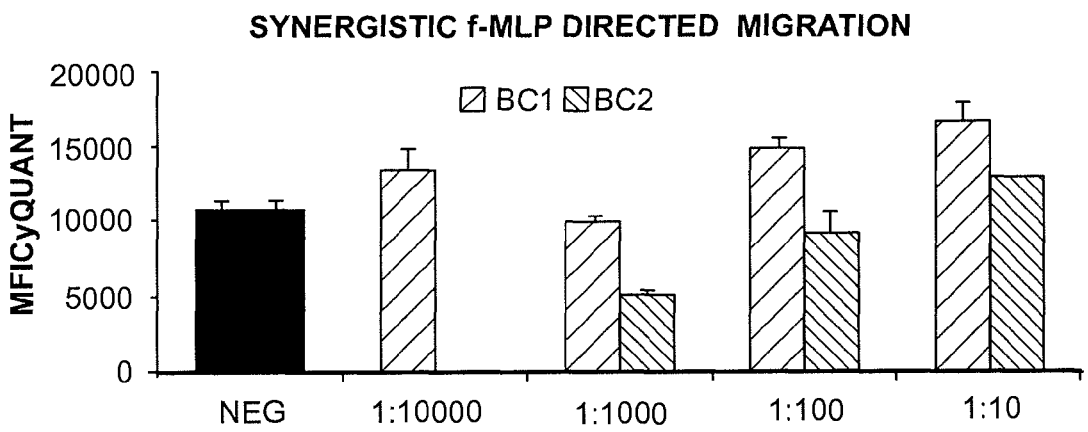
FIG. 9 is a bar chart illustrating synergistic f-MLP-directed migration showing the migratory patterns of PMN's exposed to either *Bacillus coagulans* supernatant (BC1) or *Bacillus coagulans* cell wall components (BC2) acting as a chemoattractant in the bottom chamber of the trans-well migration plate.

As shown in FIG. 9, the two *Bacillus coagulans* fractions had very different effects on the f-MLP directed migration. Higher doses of BC1 enhanced the f-MLP directed migratory activity. The chemoattractant effect of BC1 (1:10) increased migration by 55% (P<0.01). With the exception of the highest dose of BC2, this fraction reduced migration towards f-MLP. The interaction of PMN cells with BC2 made the cells much less responsive to f-MLP. BC2 (1:1000) treated cells inhibited migration by 52% (P<0.001).

Figure 10:
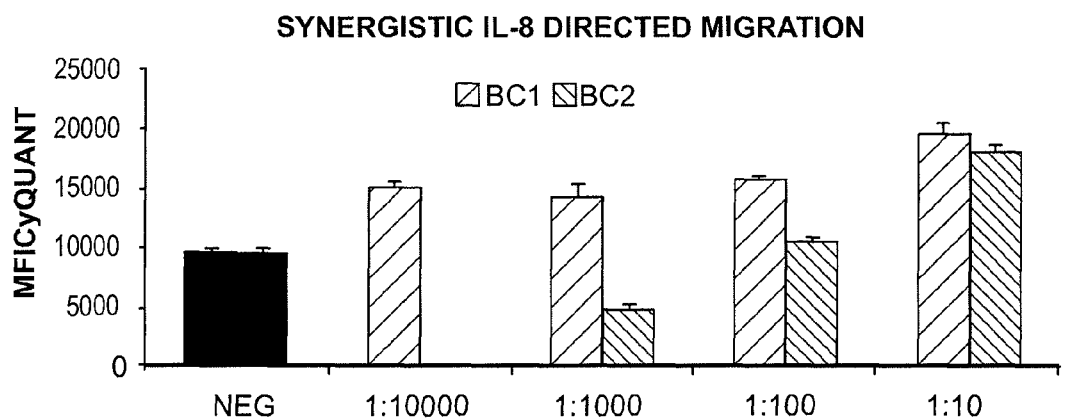
FIG. 10 is a bar graph demonstrating the synergistic IL-8-directed migration showing the migratory patterns of PMN's exposed to either *Bacillus coagulans* supernatant (BC1) or *Bacillus coagulans* cell wall components (BC2) acting as a chemoattractant in the bottom chamber of the trans-well migration plate.

As shown in FIG. 10, the two *Bacillus coagulans* fractions also had very different effects on the IL-8 directed migration. All doses of BC1 enhanced the IL-8 directed migratory activity. The chemoattractant effect of BC1 (1:10) was statistically significant (P<0.00001). BC2 had a dual effect. At higher doses BC2 enhanced IL-8 induced migration. However, at the lowest dose tested, this fraction reduced migration towards IL-8. The interaction of PMN cells with BC2 made the cells much less responsive to IL-8. BC2 (1:1000) treated cells inhibited migration by 49% (P<0.004).

Figure 11:
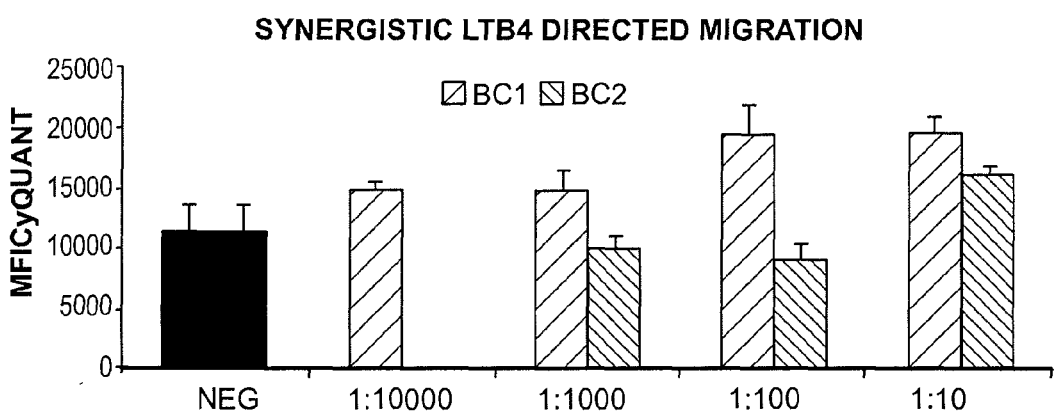
FIG. 11 is a bar chart demonstrating the synergistic LTB4-directed migration showing the migratory patterns of PMN's exposed to either *Bacillus coagulans* supernatant (BC1) or *Bacillus coagulans* cell wall components (BC2) acting as a chemoattractant in the bottom chamber of the trans-well migration plate.

As shown in FIG. 11, the two *Bacillus coagulans* fractions also had very different effects on the LTB4 directed migration. All doses of BC1 enhanced the LTB4 directed migratory activity. The chemoattractant effect of BC1 (1:10) was statistically significant (P<0.002).

BC2 had a dual effect. At the higher dose, it enhanced LTB4 induced migration. However, at the 1:100 dose, this fraction reduced migration towards LTB4. The interaction of PMN cells with BC2 made the cells less responsive to LTB4. BC2 (1:100) treated cells inhibited migration by 11% (P<0.01).

Effect on Macrophage Phagocytic Activity

Phagocytosis of microbial particles is an important part of the innate immune response. It is a rapid process, and the effect of a test product on enhancing this cellular function can be almost immediate. Phagocytosis was measured by how well PMN cells engulfed green fluorescent carboxylated fluorospheres. The mean fluorescence intensity (MFI) of phagocytic cells was then evaluated by flow cytometry. Freshly purified peripheral blood mononuclear cells were pretreated with either *Bacillus coagulans* supernatant (BC1) or *Bacillus coagulans* cell wall components (BC2) for 3 minutes, and then introduced to fluorescent micro-particles mimicking bacteria. The cells were allowed to ingest particles for 2 minutes, after which free micro-particles were removed by centrifugation. The fluorescence intensity of the phagocytes was then evaluated by flow cytometry. Electronic gating was performed on the monocyte population, and the analysis was performed by measuring the mean fluorescence intensity (MFI FL3). A faster or stronger rate of phagocytosis results in a higher number of fluorescent micro-particles per cell.

Figure 12:
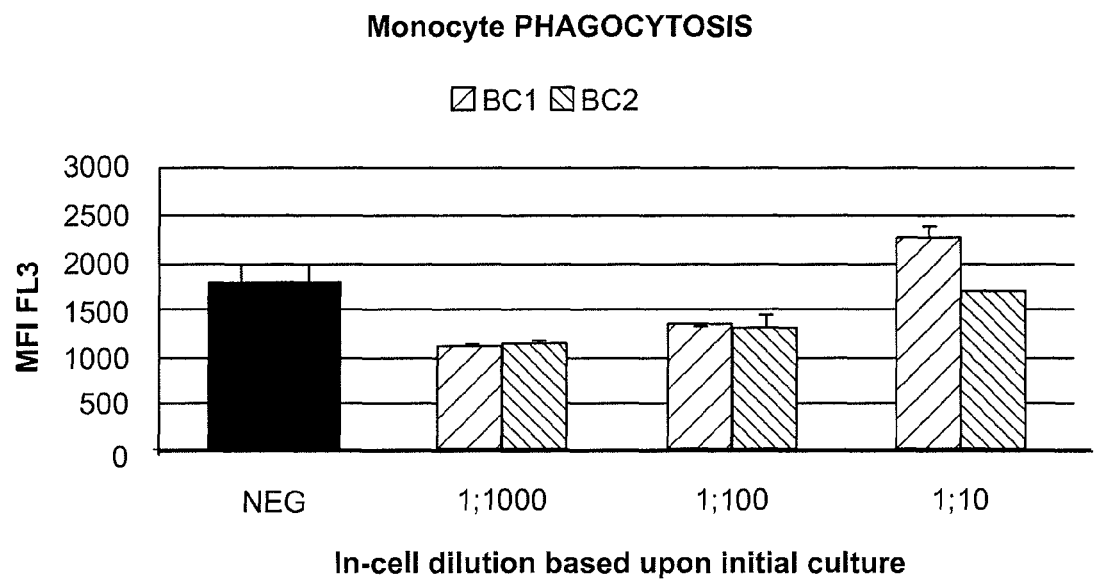
FIG. 12 is a bar graph illustrating the monocyte phagocytosis as measured by how well the monocyte can ingest green carboxylate fluorspheres.
Figure 13:
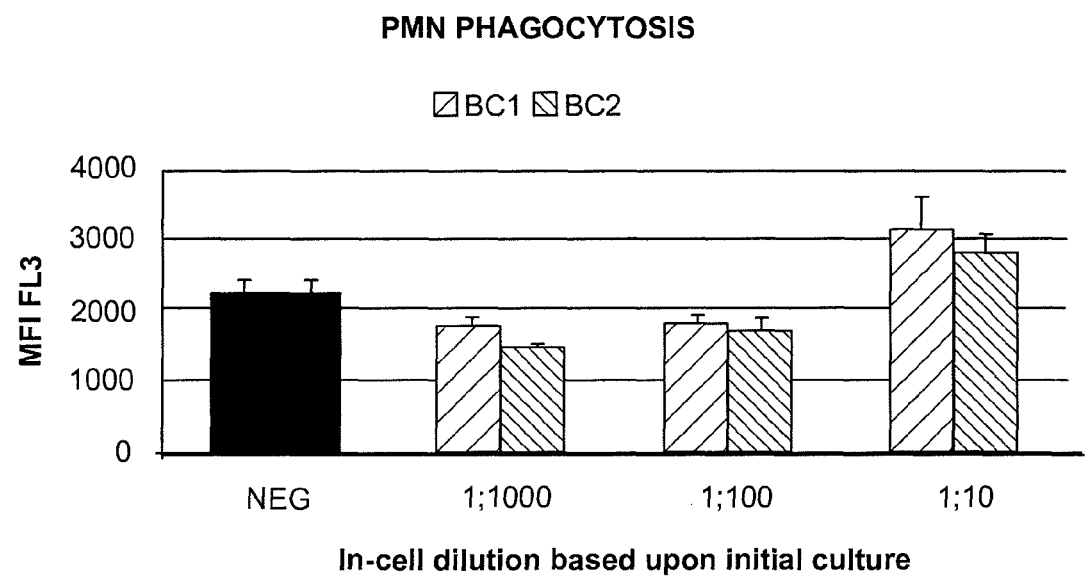
FIG. 13 is a bar chart demonstrating PMN phagocytosis as measured by how well the monocyte can ingest green carboxylate fluorspheres.

As shown in FIG. 12, BC1 at the dilution of 1:10 increased monocyte phagocytosis. This increase of 28% was highly significant (P<0.01). As shown in FIG. 13, BC1 and BC2 increased phagocytosis in PMN cells compared to the negative controls. Exposure of PMN cells to BC1 at the 1:10 dilution increased phagocytosis by 40% (p<0.02). Exposure of PMN cells to BC2 at the 1:10 dilution increased phagocytosis by 25% (p<0.008). Further dilutions of both products resulted in reduced PMN phagocytosis (p<0.05).

Figure 30A:
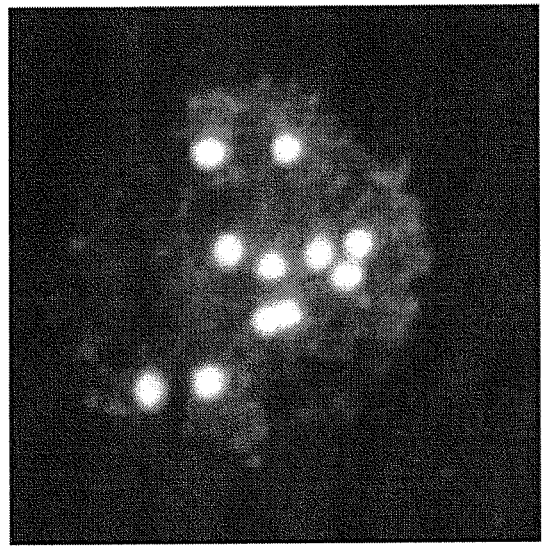
FIG. 30A is a photomicrograph depicting an untreated PMN cell that has engaged in phagocytosis. The green beads are carboxylated fluorospheres that mimic bacterial particles.
Figure 30B:
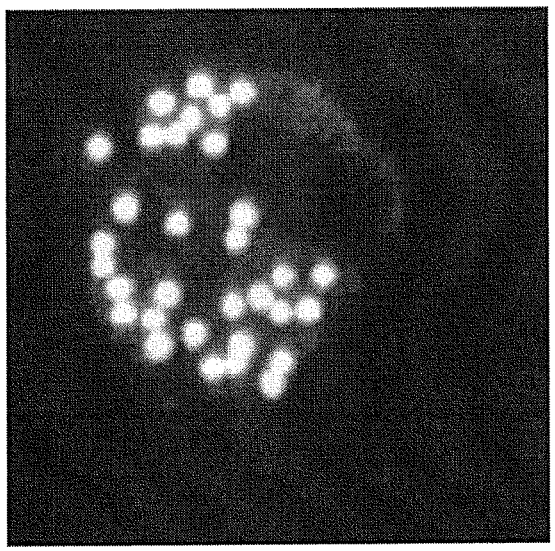
FIG. 30B is a photomicrograph depicting a PMN cell treated with *Bacillus coagulans* cell wall components (BC2).

The images in FIGS. 30A and 30B represent photographs taken from a fluorescence microscope. The control shows an untreated PMN cell that has engaged in phagocytosis (FIG. 30A). The green beads are carboxylated fluorospheres that mimic bacterial particles. FIG. 30B shows a PMN cell that has been treated with BC2. This cell has ingested many more fluorospheres than the untreated cell in FIG. 30A. This figure, in combination with the data above, indicates that *Bacillus coagulans* increases the capacity of phagocytes for engulfing foreign material.

EXAMPLE 5

Activation of NK Cells

Natural Killer (NK) cells are involved in the primary defense mechanisms against transformed cells and viruses. These cells travel in the blood stream in a state of rest, but can be immediately activated to a) kill cancer cells by either cell contact or secretion of cytotoxic compounds such as perforin and granzyme, b) proliferate, and c) secrete substances that attract other cells into the site. In order to investigate a possible effect of BC1 and BC2 on NK cell activation, the changes in expression of the NK activation cell surface marker CD69 were examined. The increased expression of this marker has been associated with an increased cytotoxic activity of NK cells (Clausen et al, 2003 Immunobiol, 207 (2):85-93).

Freshly purified human peripheral blood mononuclear cells were used for these assays. The cells were plated in 96-well micro-assay plates in triplicate. Negative control wells in triplicate were left untreated. Positive controls were treated with IL-2 at a dose of 100 international units per mL (IU/mL). After 18 hours of culture, cells were stained for the activation molecule CD69 and the growth factor receptor CD25 on the surface of CD3-negative, CD56-positive NK cells, and on CD3-positive, CD56-positive NKT lymphocytes to evaluate activation of NK and/or NKT cells in vitro.

Figure 14:
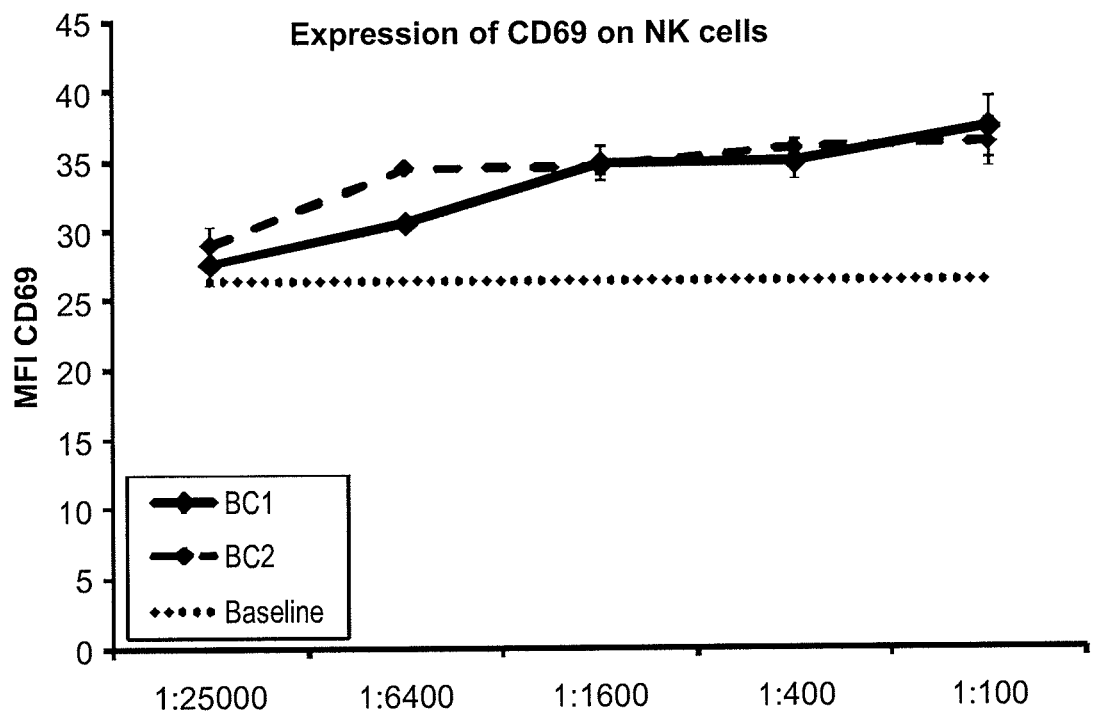
FIG. 14 is a line graph showing cluster of differentiation 69 (CD69) expression of natural killer (NK) cells (analysis generated by measuring the mean fluorescence intensity (MFI) of CD69).

FIG. 14 depicts the change in mean fluorescence intensity of the NK activation marker CD69, following exposure of NK cells to either *Bacillus coagulans* supernatant (BC1) or *Bacillus coagulans* cell wall components (BC2). Both BC1 and BC2 showed a clear dose-dependent induction of the expression of CD69 on NK cells. The effect reached high statistical significance for both BC1 and BC2 at a 1:400 dilution, where CD69 expression was increased by 32% (p<0.01) for BC1, and by 36% for BC2 (p<0.003).

Figure 15:
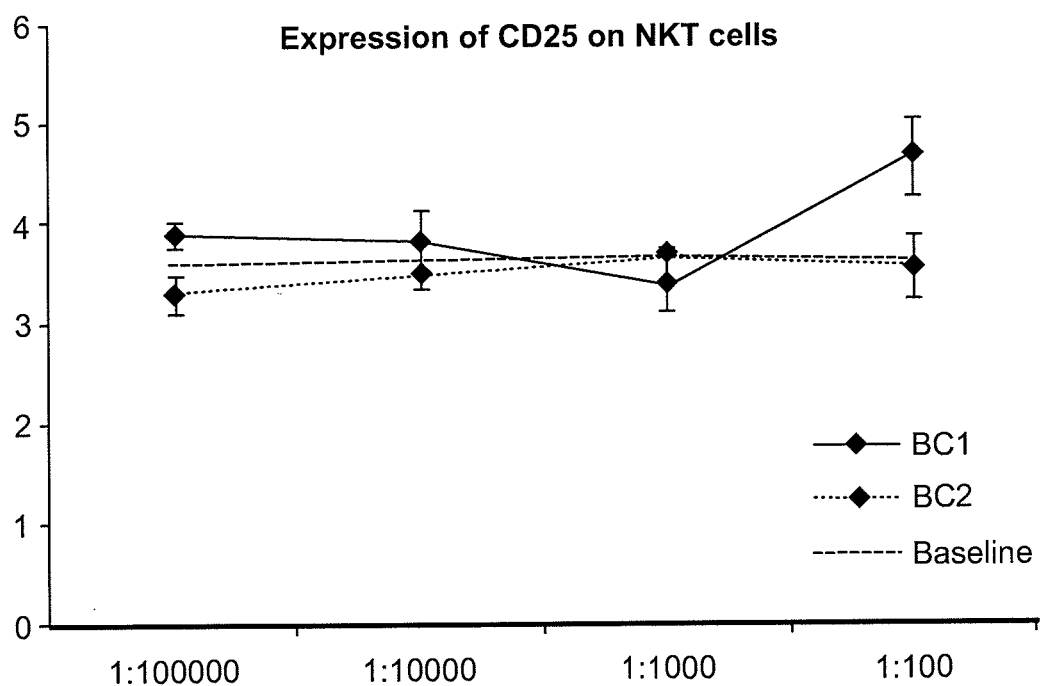
FIG. 15 is a line graph showing CD25 expression of NKT cells (analysis generated by measuring the MFI of CD25).

FIG. 15 shows the expression of CD25 on NKT cells. For both BC1 and BC2, there was not a large difference in CD25 expression compared to baseline levels. While the 1:100 dilution of BC1 resulted in an increase in expression, this change did not reach statistical significance. No changes in CD25 expression on T cells were observed when comparing untreated cells to those treated with either BC1 or BC2.

Externalization of CD 107a on NK Cells in Response to Tumor Cells

One of the functions of NK cells is to kill tumor cells and virus-infected cells via cell-cell contact and by secretion of substances such as Perforin. During this process, the CD 107a receptor expressed on the interior of granules in the cytoplasm of NK cells is transiently brought to the cell surface. Thus, CD 107a expression on NK cells is a measure of their cytotoxic activity by secretion of cytotoxic substances.

Freshly-purified human peripheral blood mononuclear cells were used for this assay. The cells were plated in round-bottom 96-well micro-assay plates, and treated with serial dilutions of the test products in triplicate. Negative control wells in triplicate were left untreated. All other wells were used for addition of the NK-cell sensitive K562 tumor cell line, widely used in NK cell cytotoxicity assays. Positive control wells were left without adding test products. All remaining wells were treated with serial dilutions of test products. The two cell types were brought physically together by a brief 15-seconds centrifugation, and incubated for 45 minutes at 37° C. Cells were transferred to V-bottom microtiter plates for processing and staining. The expression of CD107a on the NK cells was analyzed by flow cytometry, where the NK cells were differentiated from the other lymphocytes based on positive staining for CD3 and CD56, and from the K562 cells based on size. Cytotoxic activity of NK cells in vitro was measured. The response in this assay predicts a similar response to non-malignant, virally infected cells.

Figure 16:
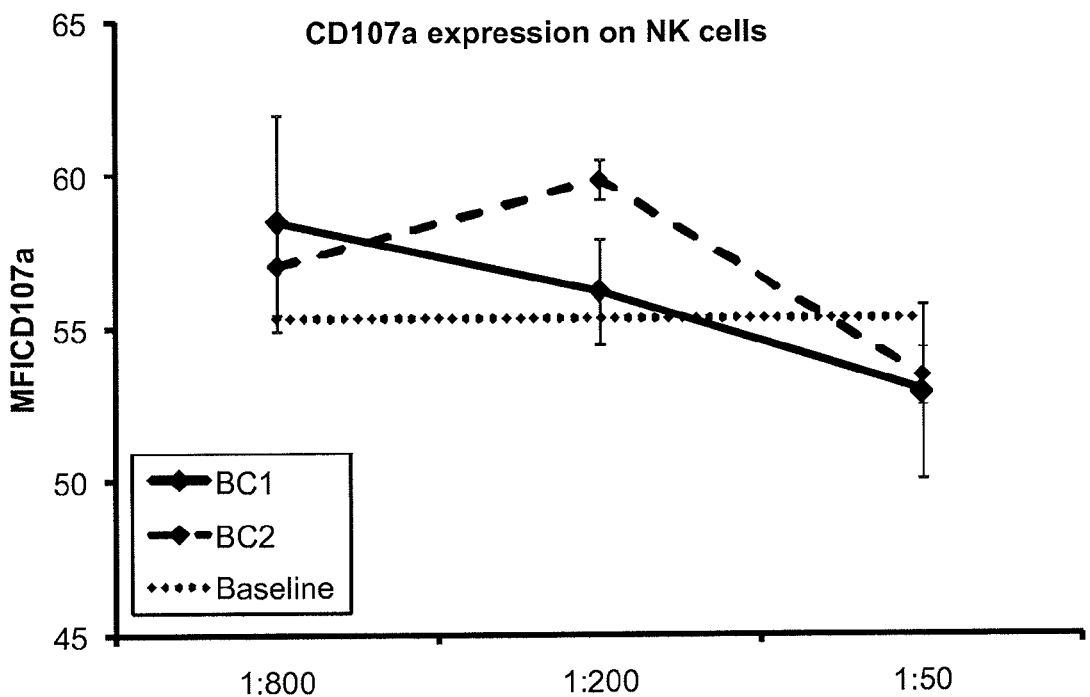
FIG. 16 is a line graph demonstrating CD107a expression of NK cells (analysis generated by measuring the MFI of CD 107a).

FIG. 16 shows the change in mean fluorescence intensity (MFI) of CD107a expression on natural killer cells that have been exposed to tumor cells, with or without the addition of BC1 or BC2. Both BC1 and BC2 show a mild increase in CD107a cell surface expression, with BC2 having the strongest effect at the 1:200 dilution; the effect did not quite reach statistical significance (p<0.07).

EXAMPLE 6

Support of Adaptive Immune Function: Modulation of Lymphocyte Proliferation and Cytokine Production in Response to Two Known Mitogens A series of assays were performed to determine if the test products would trigger exaggerated immune reactions. As part of a standard safety testing of natural products, test products were examined for mitogenic potential, that is, whether they induce cell division in healthy human lymphocytes. Simultaneous to the test of mitogenic potential, the test products were examined for their effect on cells responsible for the adaptive immune defense, that is, T and B lymphocytes. The lymphocyte proliferation assay offers a simple method to assess whether the compositions alter lymphocyte responsiveness to known signals. A change in the proliferative response to known mitogens in the presence of a composition indicates an immunomodulatory effect, such as T and B lymphocyte signaling and activation.

The compositions were tested in serial dilutions in the presence and absence of mitogens. Two mitogens were tested in parallel: Phytohemagglutinin (PHA), which is a T cell mitogen that will induce T cell proliferation, and Pokeweed Mitogen (PWM), which is a mitogen that requires the collaboration of T cells, B cells and monocytes in the culture. The PHA is a cleaner signal, but the PWM is a more physiological signal.

Freshly purified human peripheral blood mononuclear cells (PBMC) were cultured in the absence versus presence of serial dilutions of the compositions. Three parallel sets of cultures were established, where one tested the direct effect of test product on lymphocyte proliferation, and the two others examined the interference of the composition with response to the known mitogens. Positive controls included cells treated only with a mitogen in the absence of test product. A change (increase, decrease) of mitogen-induced proliferation is a strong indication of the presence of immunomodulating compounds.

Neither BC1 nor BC2 had a mitogenic effect on lymphocyte proliferation following five days incubation at 37° C. with product and culture media.

Figure 17:
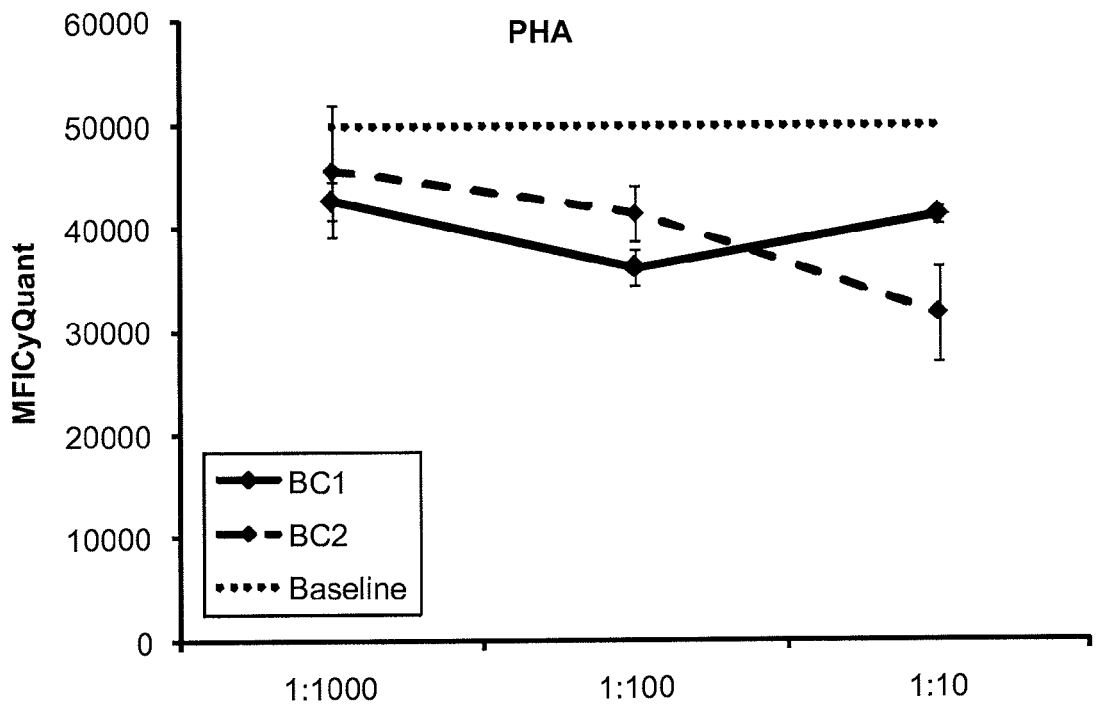
FIG. 17 is a line graph illustrating the results of lymphocytes that were pre-treated with either *Bacillus coagulans* supernatant (BC1) or *Bacillus coagulans* cell wall components (BC2) and then exposed to the mitogen phytohemagglutinin (PHA).
Figure 18:
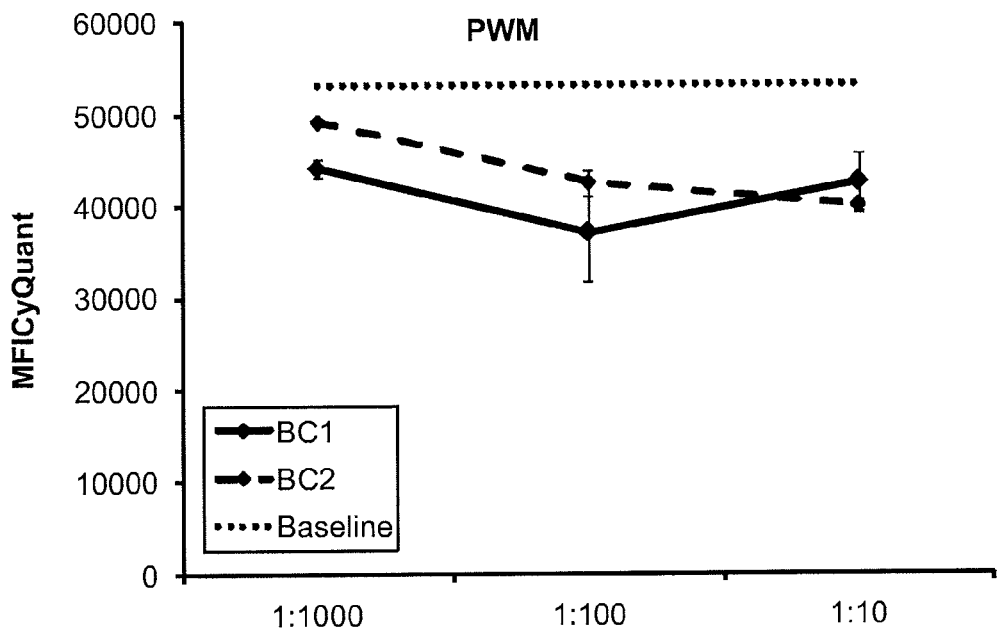
FIG. 18 is a bar graph demonstrating the results of lymphocytes that were pre-treated with either *Bacillus coagulans* supernatant (BC1) or *Bacillus coagulans* cell wall components (BC2) and then exposed to the pokeweed mitogen (PWM).

Both BC1 and BC2 showed a reduction in lymphocyte proliferation in the presence of PHA and PWM (FIGS. 17 and 18). This reduction was significant at all doses of BC1 in the presence of both PHA and PWM ($p<0.02$) and was significant for the two highest concentrations of BC2 ($p<0.02$). Additionally, high statistical significance was reached for BC1 at the 1:10 ($p<0.003$) and 1:100 ($p<0.002$) doses and BC2 at the 1:10 ($p<0.004$) dose in the presence of PHA and BC1 at the 1:100 ($p<0.005$) dose and BC2 at the 1:10 ($p<0.002$) and 1:100 ($p<0.006$) doses in the presence of PWM.

Cytometric Bead Array

Figure 19A:
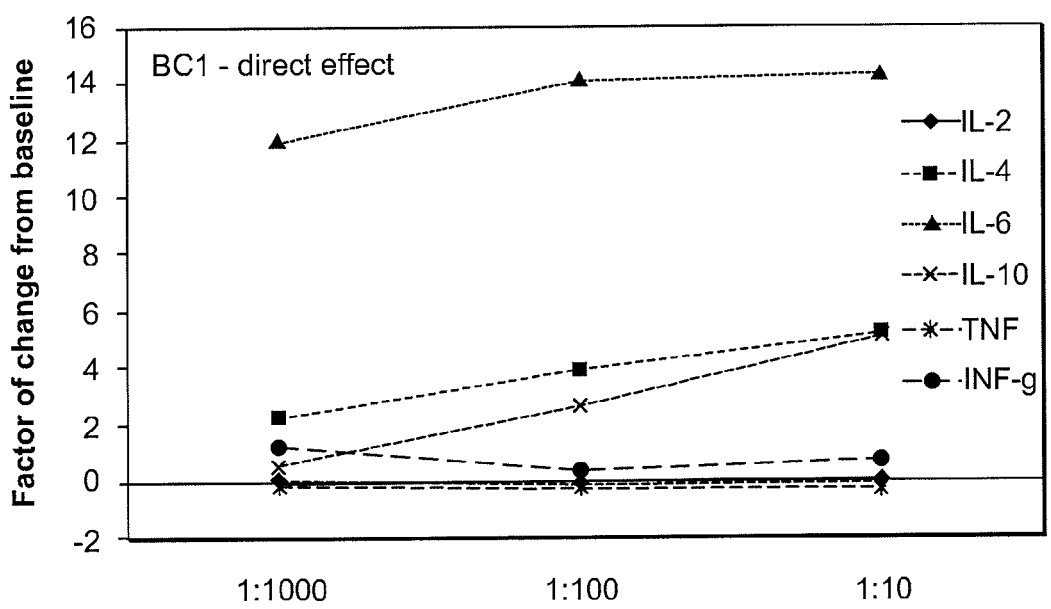
FIGS. 19A and B are line graphs showing the cytokine production of lymphocytes pre-treated with *Bacillus coagulans* supernatant (BC1).
Figure 19B:
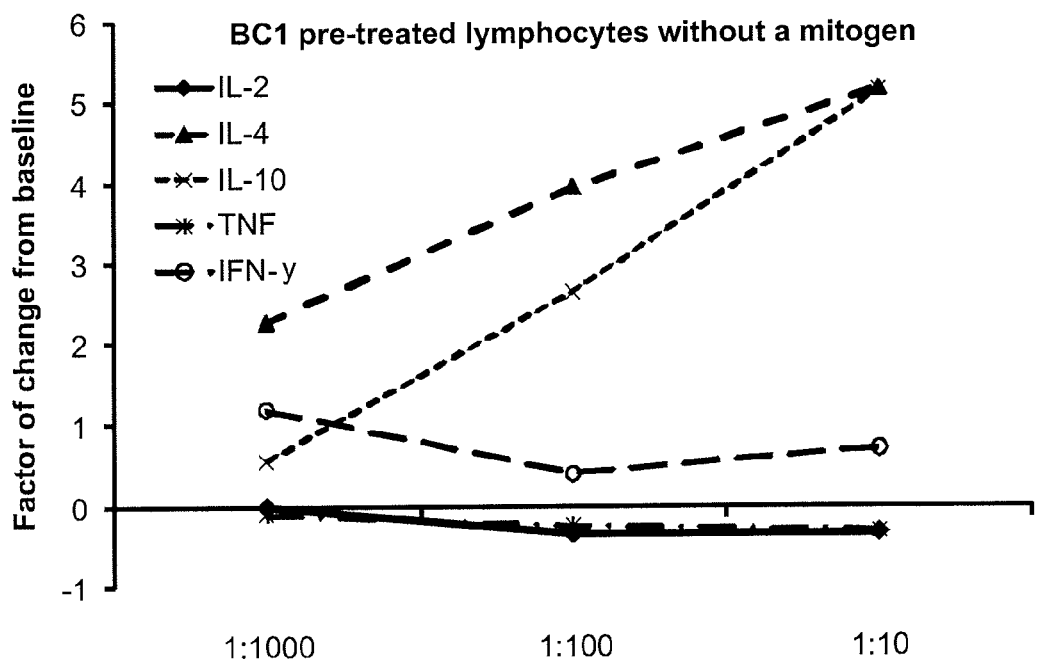
Figure 20A:
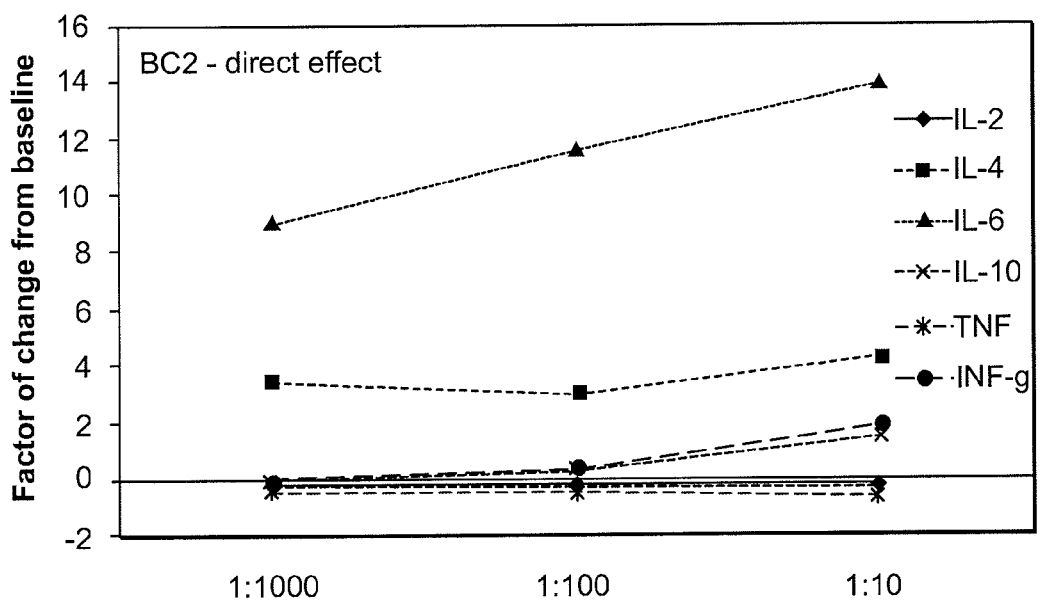
FIGS. 20A and B are line graphs illustrating the cytokine production of lymphocytes pre-treated with *Bacillus coagulans* cell wall components (BC2).
Figure 20B:
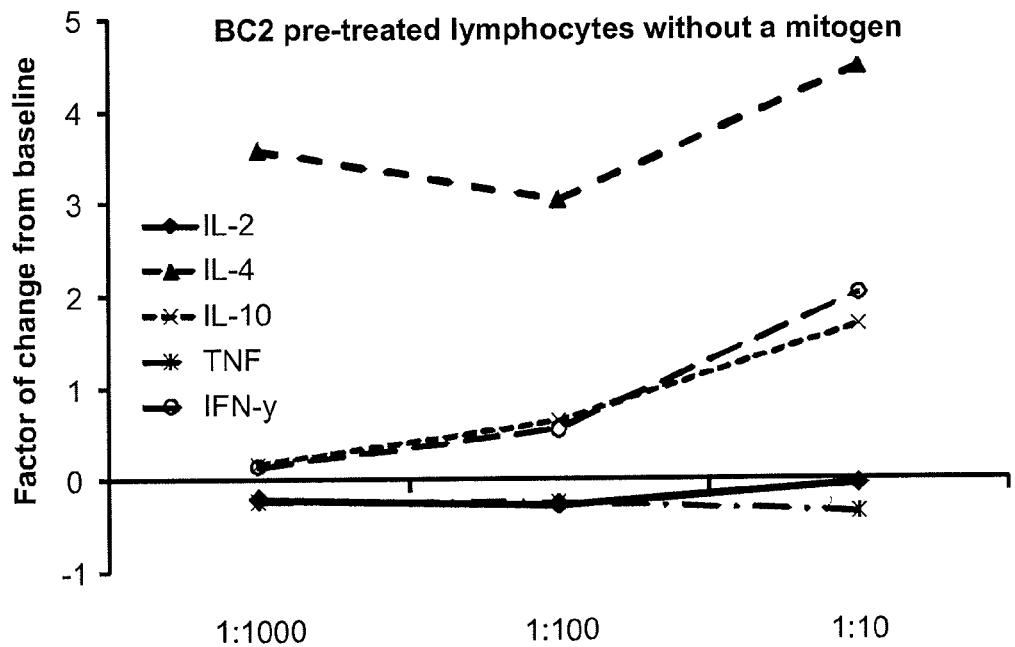

A flow cytometry-based Th1/Th2 cytokine bead array (CBA) for the 6 cytokines IL-2, IL-4, IL-6, IL-10, TNF-α and INF-γ was used to evaluate the levels of cytokines present in the supernatants from 5-day lymphocyte cultures. In FIGS. 19-20, relative changes in cytokine concentrations are first presented in overview graphs showing changes in all 6 cytokines across the 3 product dilutions. There are separate graphs for BC1 and BC2 and changes are represented as factor of change from baseline (lymphocytes cultured without product).

Lymphocytes were also cultured (with or without product) in the presence of 2 different mitogens. Phytohemagglutinin (PHA) was used to induce T cell proliferation, and Pokeweed Mitogen (PWM) was used to induce T and B lymphocyte proliferation in a process that requires the collaboration of T cells, B cells, and monocytes in the culture. Comparisons were made between lymphocytes cultured in the presence of no product and lymphocytes cultured in the presence of 1:100 dilutions of either BC1 or BC2. This data is presented in separate graphs for each individual cytokine and also compares changes in cytokine levels in lymphocytes that were cultured without mitogens either without product or with the 1:100 dilutions of BC1 and BC2.

Figure 21:
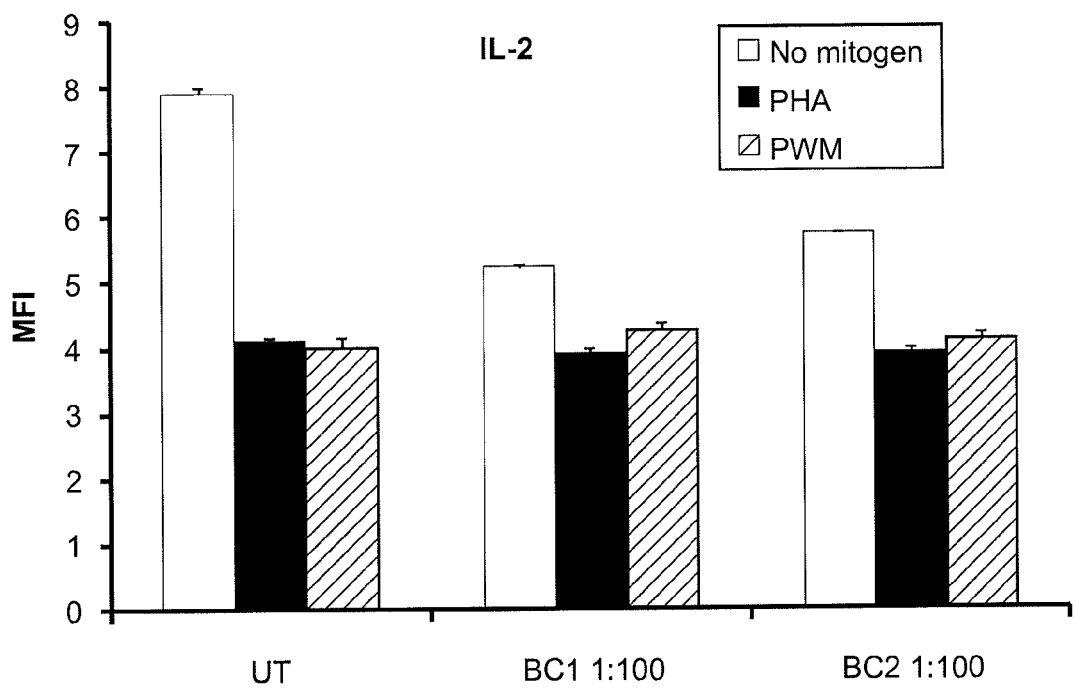
FIG. 21 is a bar chart showing the results of lymphocytes that were pre-treated with either *Bacillus coagulans* supernatant (BC1) or *Bacillus coagulans* cell wall components (BC2), and then exposed to no mitogen, PHA, or PWM. This graph represents relative levels of the cytokine IL-2 present in the supernatant of 5 day lymphocyte cultures. Untreated (UT).

In the absence of mitogens, both BC1 and BC2 treatment of PBMC led to decreased IL-2 levels compared to untreated PBMC (FIG. 21). This reduction was statistically significant for BC1 and BC2 ($p<0.002$). No statistically significant changes in IL-2 levels were observed with BC1 or BC2 treatment in the presence of either mitogen, compared to BC1 versus BC2 treatment alone.

Figure 22:
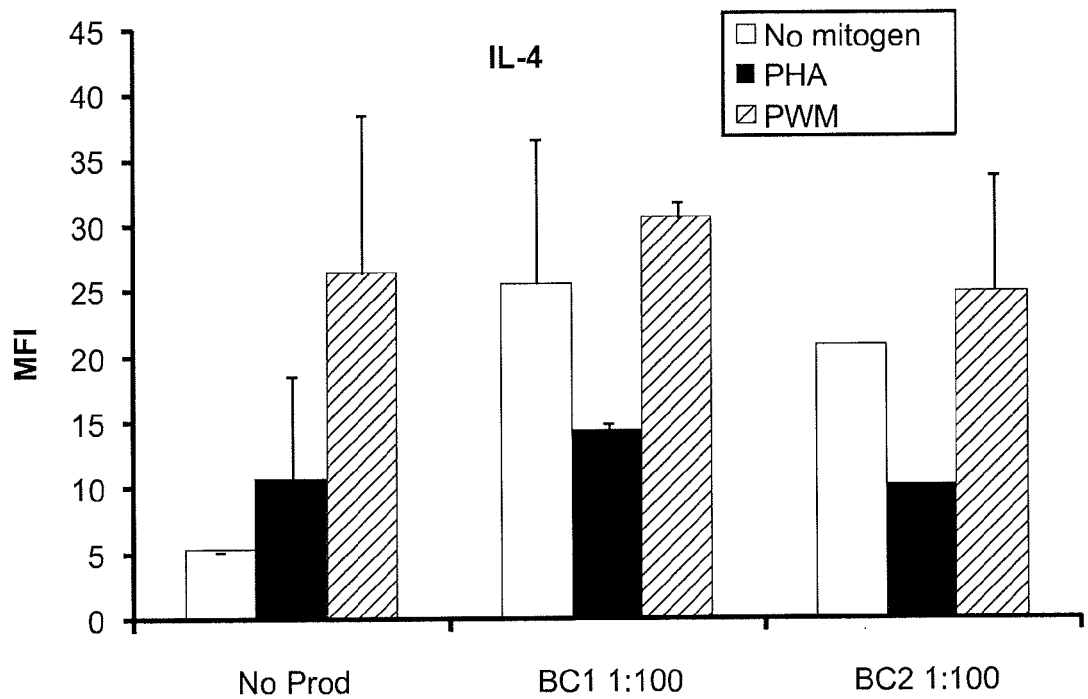
FIG. 22 is a bar graph illustrating the results of lymphocytes that were pre-treated with either *Bacillus coagulans* supernatant (BC1) or *Bacillus coagulans* cell wall components (BC2) and then exposed to no mitogen, PHA, or PWM. This graph represents relative levels of the cytokine IL-4 present in the supernatant of 5 day lymphocyte cultures.

In the absence of mitogens, both BC1 and BC2 treatment of PBMC led to increased IL-4 levels compared to untreated PBMC (FIG. 22). This increase was statistically significant for both BC1 ($p<0.002$) and BC2 ($p<0.01$). No statistically significant changes in IL-4 levels were observed with BC1 or BC2 treatment in the presence of either mitogen, compared to BC1 versus BC2 treatment alone.

Figure 23:
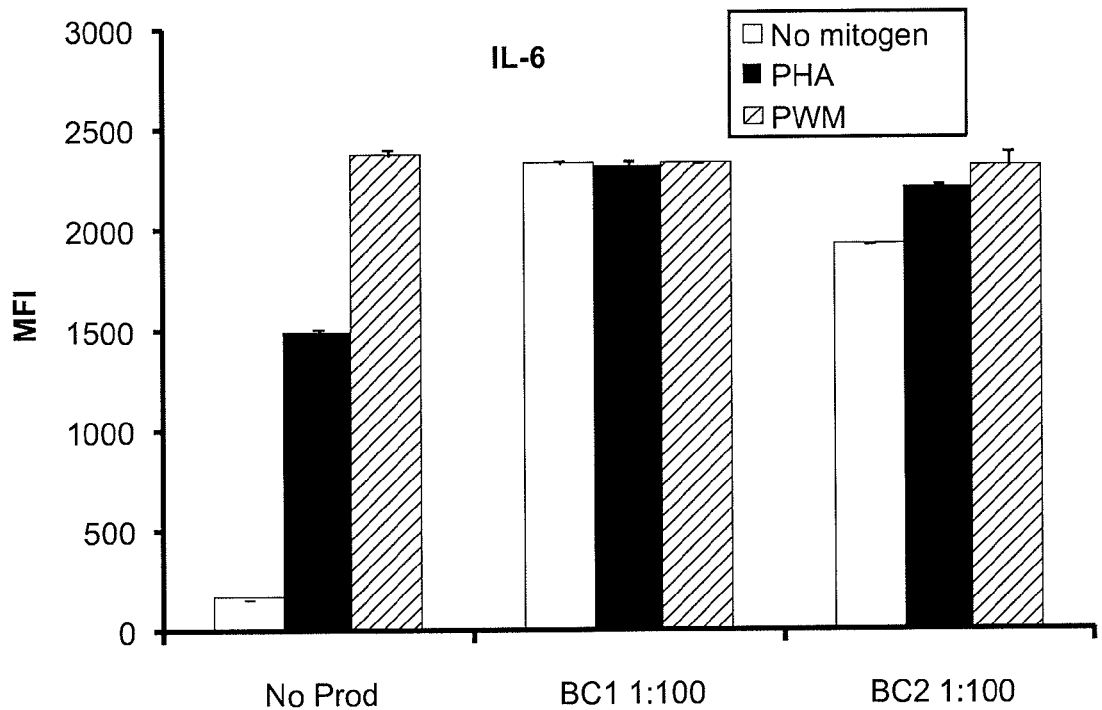
FIG. 23 is a bar chart demonstrating the results of lymphocytes pre-treated with either *Bacillus coagulans* supernatant (BC1) or *Bacillus coagulans* cell wall components (BC2), and then exposed to no mitogen, PHA, or PWM. This graph represents relative levels of the cytokine IL-6 present in the supernatant of 5 day lymphocyte cultures.

As shown in FIG. 23, both BC1 and BC2 treatment of PBMC, in the absence of mitogens, led to massive induction of IL-6 production. The increase was highly statistically significant ($P<0.00002$). No statistically significant changes in IL-6 levels were observed with BC1 or BC2 treatment in the presence of Pokeweed mitogen, compared to BC1 versus BC2 treatment alone. The IL-6 induction by both BC1 ($P<0.001$) and BC2 ($P<0.0009$) was found to be highly statistically significant.

Figure 24:
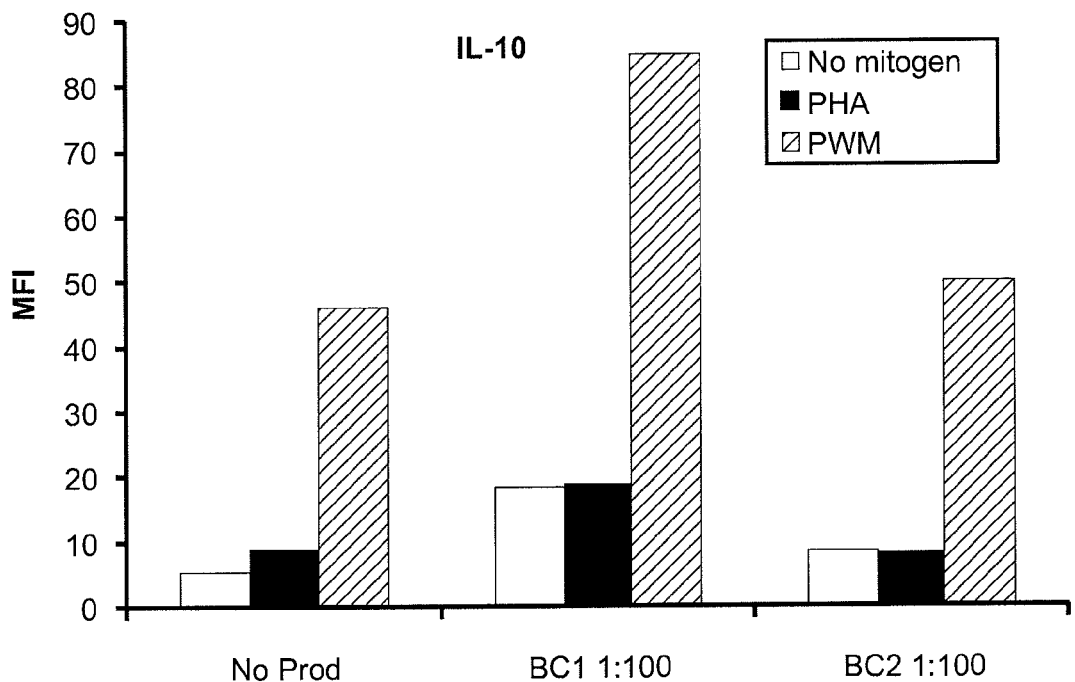
FIG. 24 is a bar graph illustrating the results of lymphocytes that were pre-treated with either *Bacillus coagulans* supernatant (BC1) or *Bacillus coagulans* cell wall components (BC2), and then exposed to no mitogen, PHA, or PWM. This graph represents the relative levels of the cytokine IL-10 present in the supernatant of 5 day lymphocyte cultures.

As shown in FIG. 24, both BC1 and BC2 treatment of PBMC, in the absence of mitogens, led to induction of IL-10 production. The increase was highly significant ($P<0.008$). PBMC treated with both BC1 and PHA led to higher IL-10 production ($P<0.0009$) than if cells were treated with either product alone. Treatment of PBMC with BC1 and PWM also led to an increase in IL-10 production; however, the data was not found to be statistically significant. No statistically significant changes in IL-6 levels were observed with BC2 treatment in the presence of either mitogen when compared to BC2 treatment alone.

Figure 25A:
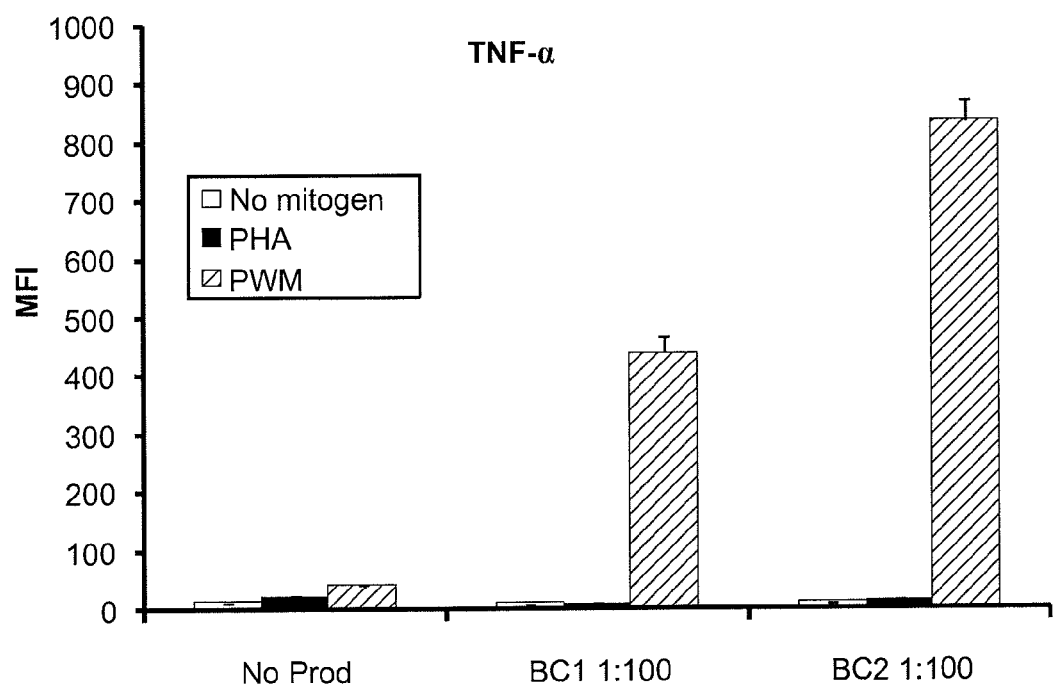
FIGS. 25A and B shows a series of bar charts showing the results of lymphocytes that were pre-treated with either *Bacillus coagulans* supernatant (BC1) or *Bacillus coagulans* cell wall components (BC2), and then exposed to no mitogen, PHA, or PWM. This graph represents the relative levels of the cytokine TNF-α present in the supernatant of 5 day lymphocyte cultures.
Figure 25B:
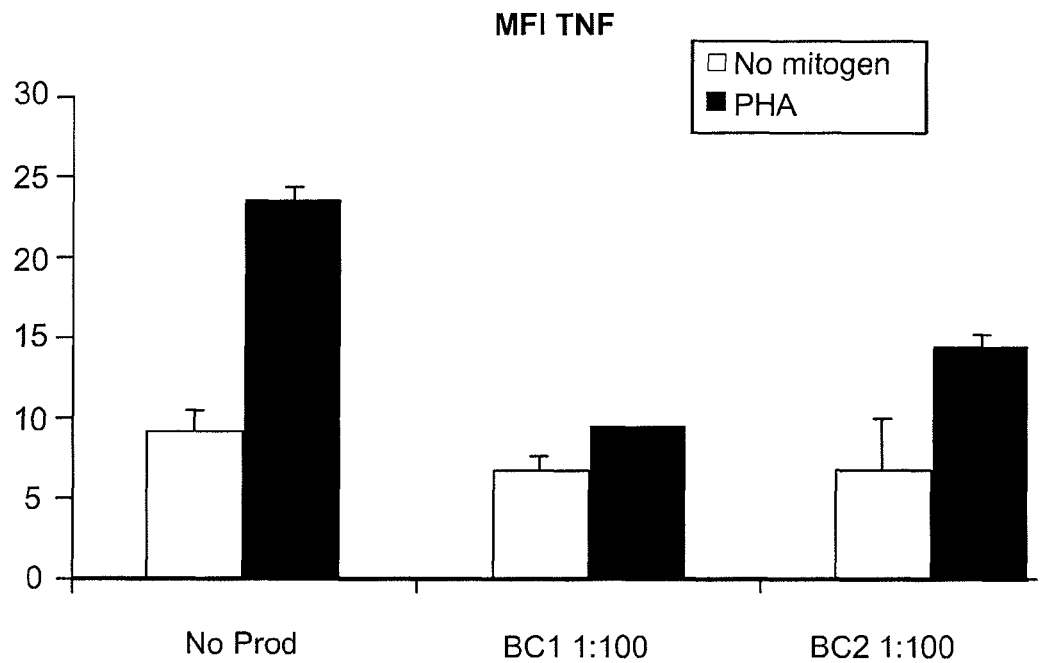

In the absence of mitogens, TNF-α production was slightly lower than untreated PBMC in the presence of both BC1 and BC2 (FIGS. 25A and 25B). This mild reduction was not statistically significant for either BC1 or BC2. Treatment of PBMC with either BC1 or BC2 in the presence of PHA resulted in 2-fold decreases in TNF-α expression that were statistically significant for both BC1 ($P<0.002$) and BC2 ($P<0.006$). In contrast, treatment of PBMC with BC1 and BC2 in the presence of PWM resulted in strong increases in TNF-α levels. In the presence of PWM, BC1 treatment produced an 11-fold increase ($P<0.003$) and BC2 treatment a 22-fold increase ($P<0.001$).

Figure 26A:
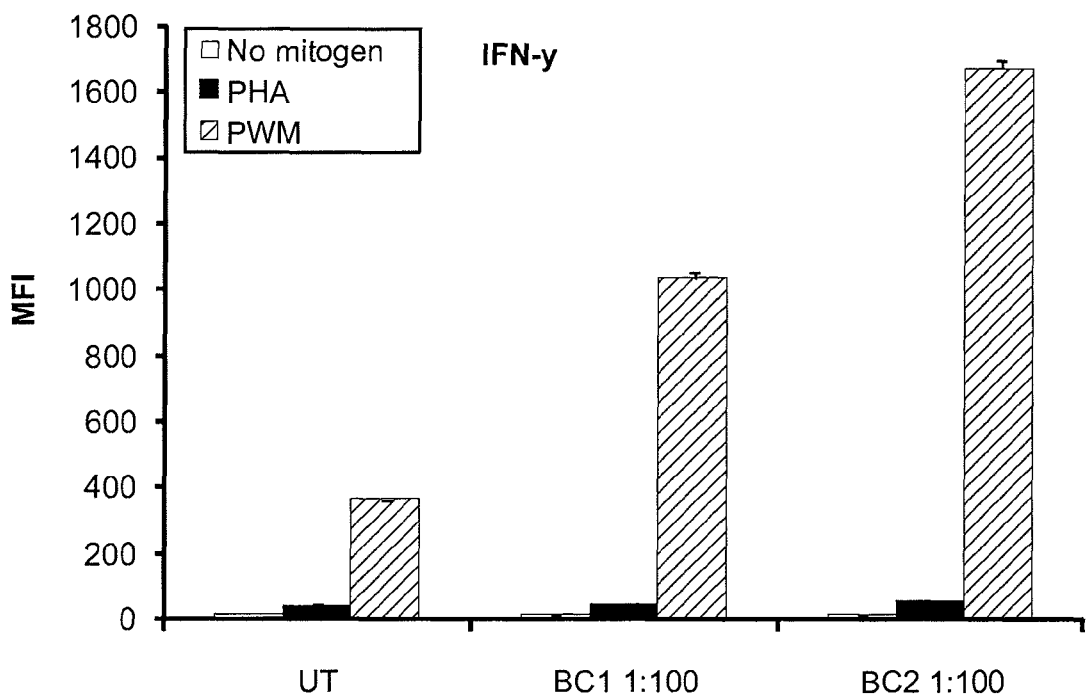
FIGS. 26A and B show a series of bar charts showing the results of lymphocytes that were pre-treated with either *Bacillus coagulans* supernatant (BC1) or *Bacillus coagulans* cell wall components (BC2), and then exposed to no mitogen, PHA, or PWM. This graph represents relative levels of the cytokine IFN-γ present in the supernatant of 5 day lymphocyte cultures.
Figure 26B:
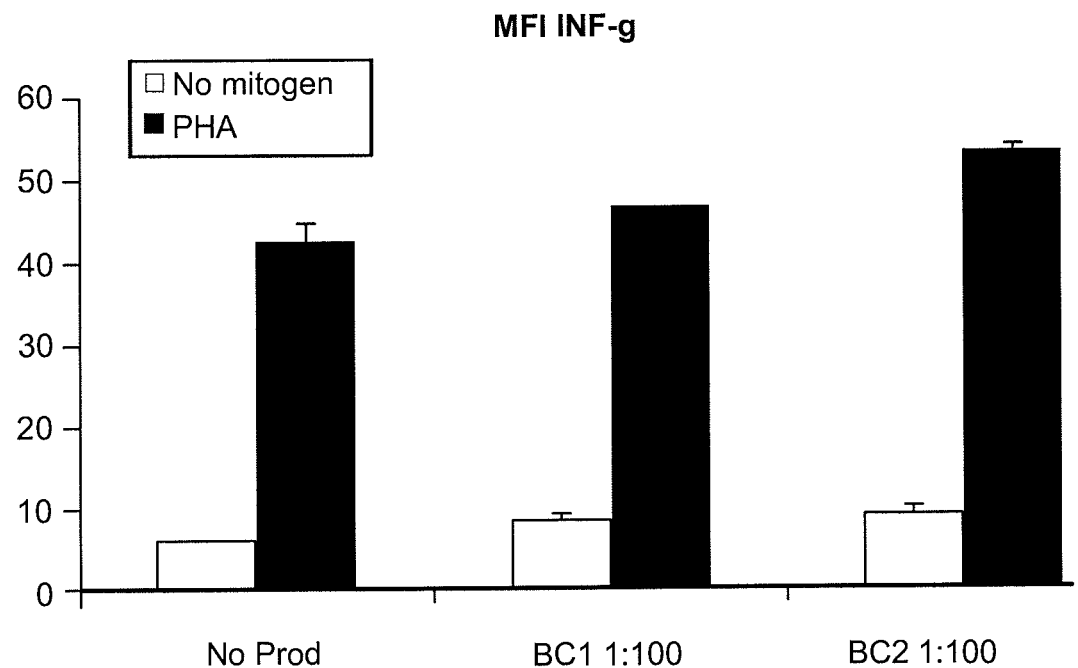

In the absence of mitogens, INF-γ levels increased in response to treatment with both BC1 and BC2 (FIGS. 26A and 26B). These changes were highly statistically significant for both BC1 ($P<0.001$) and BC2 ($P<0.0004$). Treatment of PBMC with either BC1 or BC2 in the presence of PHA did not produce statistically significant changes in INF-γ expression. In contrast, treatment of PBMC with BC1 and BC2 in the presence of PWM resulted in 3-fold (BC1) and 4-fold (BC2) increases in INF-γ levels, both of which were statistically significant ($P<0.0004$).

EXAMPLE 7

Anti-Oxidant Effects: Cell-Based Antioxidant Protection Assay

Figure 27:
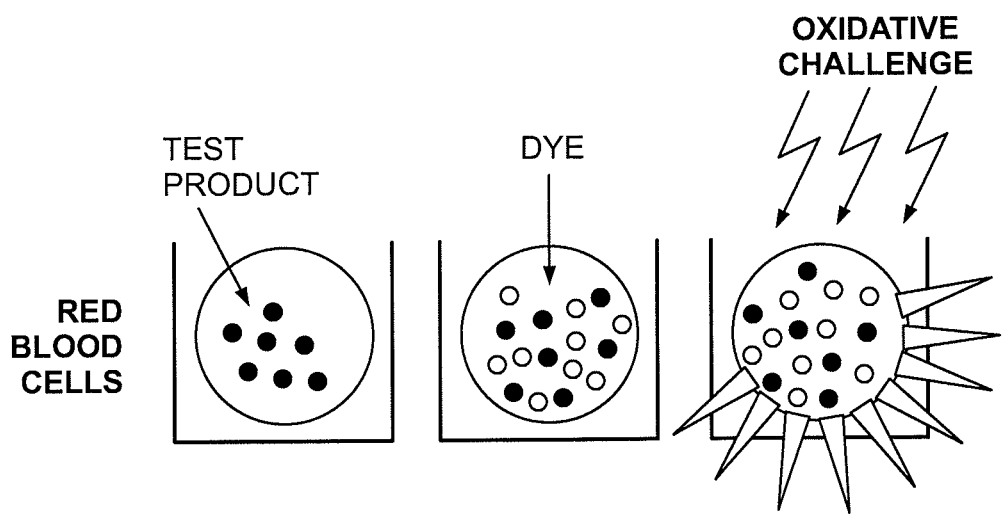
FIG. 27 is a schematic of a cell-based antioxidant protection in erythrocytes (CAP-e) representation of how a natural product gets into the cell. A dye is used to express fluorescence representing oxidative stress.
Figure 28:
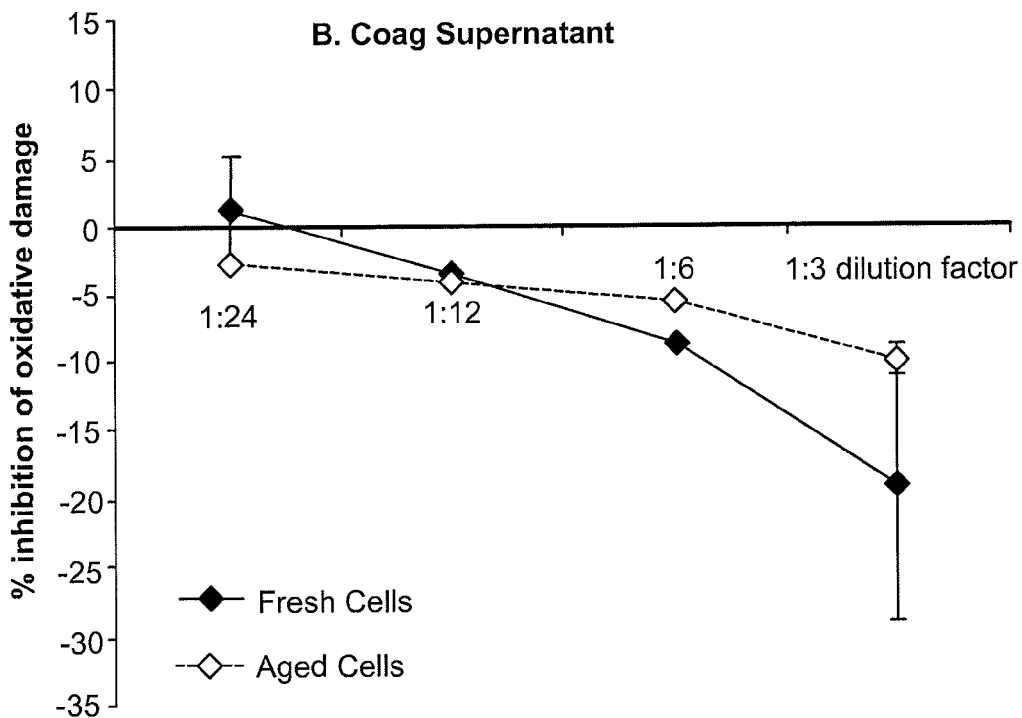
FIG. 28 is a line graph showing CAPe results for *Bacillus coagulans* supernatant being tested in parallel on fresh and aged cells.
Figure 29:
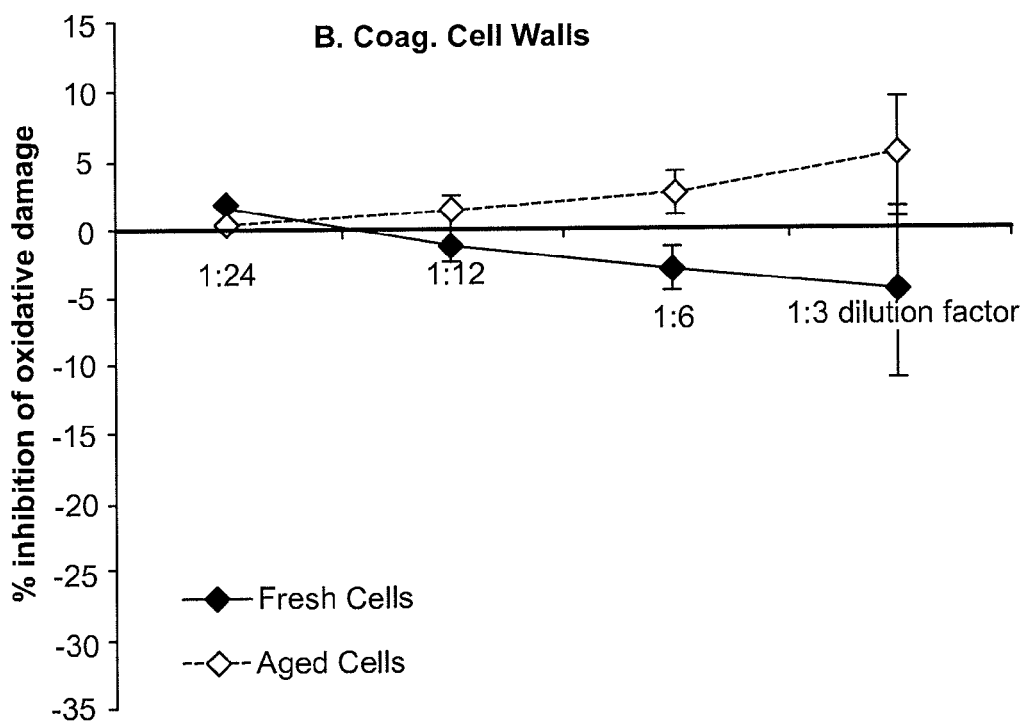
FIG. 29 is a line graph showing CAPe results for *Bacillus coagulans* cell wall being tested in parallel on fresh and aged cells.

The culture supernatant and cell wall fractions were tested in the Cell-based Antioxidant Protection in Erythrocytes (CAP-e) assay, a bioassay for antioxidants test (FIGS. 27-29). This assay allows assessment of antioxidant potential in a method that is comparable to the oxygen radical absorbance capacity (ORAC) test, but only allows measurement of antioxidants that are able to cross the lipid bilayer cell membrane.

As a model cell type, red blood cells (RBC) were used. This is an inert cell type, in contrast to other cell types such as PMN cells, where pro-inflammatory compounds may induce the reactive oxidative burst. This assay is particularly useful to assess antioxidants from complex natural products in a cell-based system.

Freshly purified human RBC were washed repeatedly in physiological saline, and then exposed to the test compositions. During the incubation with a test product, any antioxidant compounds able to cross the cell membrane can enter the interior of the RBC. RBC were then washed to remove compounds that were not absorbed by the cells, and loaded with the DCF-DA dye, which turns fluorescent upon exposure to reactive oxygen species. Oxidation was triggered by addition of the peroxyl free radical generator AAPH. The fluorescence intensity was evaluated. The low fluorescence intensity of untreated control cells serve as a baseline, and RBC treated with AAPH alone serve as a positive control for maximum oxidative damage. An observation of a reduced fluorescence intensity of RBC exposed to a test product and subsequently exposed to AAPH, indicates that the test product contains antioxidants available to penetrate into the cells and protect these from oxidative damage.

For the testing of BC1 and BC2, the antioxidant protection capacity in both freshly isolated RBC and in RBC that had been stored for 45 days was tested. Fresh RBC contain antioxidants derived from food as well as redox enzymes. With storage, the antioxidants get depleted, and the enzymatic functions may decline over time. Both BC1 and BC2 contained compounds that could enter into RBC. These compounds entered more efficiently into fresh RBC. However, the compounds from BC1 possessed no antioxidant capacity. In contrast, they interfered with the antioxidant protective mechanisms inside the RBC. A very mild antioxidant protection is seen in aged cells exposed to BC2.

Modulation of Immune Responses by Cell-Free BC Supernatants (BC-1) and Cell-Free Cell Wall Fractions (BC-2)

In summary, both BC1 and BC2 inhibited spontaneous ROS formation and reduced ROS formation when oxidative stress had been applied to PMN's. At higher concentrations, both BC1 and BC2 increased the migration of PMN cells towards a bacterial peptide, indicating an enhancement of the immune surveillance function of PMN in detecting bacteria. Conversely, at low concentrations, both BC1 and BC2 decreased the migration of PMN cells towards a bacterial peptide, indicating that at low concentrations, the compounds present in the supernatant and cell wall preparations of *Bacillus coagulans* had an immunomodulatory effect on the ability of the PMN to respond to the bacterial peptide signal. This effect underlies processes that dictate how the immune system responds to a bacterial infection vs. resident (beneficial) commensal bacteria in the gut. The highest dose of BC1 increased monocyte phagocytosis. BC2 did not increase monocyte phagocytosis. BC1 and BC2 at the strongest dose increased PMN phagocytosis. NK expression (CD69) was increased in all dilutions of BC1 and BC2 tested. BC1 and BC2 both deceased lymphocyte proliferation at all doses. Both *Bacillus coagulans* fractions reduced IL-2 and TNF. These cytokines are known TH1 cytokines which is directed at macrophage activation. However, a mild increase was noticed for IFN-γ production for both *Bacillus coagulans* fractions. Both *Bacillus coagulans* fractions increased the production of IL-4, IL-6, and IL-10. These cytokines are more directly linked to TH2 production which is used to help signal and activate B-cells, which are antigen presenting cells for the adaptive immune system. BC1 and BC2 were both capable at hindering the migration of PMN cells when directed towards the known chemoattractant IL-8. This strong anti-inflammatory effect was significant across a wide range of dilutions. *Bacillus coagulans* cell wall inhibited the migration of PMN cells when directed towards the inflammatory chemoattractant LTB4.

EXAMPLE 9

Fractionation of *Bacillus coagulans* Supernatant and Cell Wall Components

Different molecular weight compounds in *Bacillus coagulans* supernatant and cell wall components were fractionated/purified to evaluate their biological effects. Three molecular range fractions are examined for various biological activities. Preparation of the Two Test Fractions (Cell Wall and Supernatant) and Spores.

A sample of BC spores was heat-activated and inoculated in a liquid culture medium. Sample is incubated at 37° C. for 24 hours. This time period allows the formation of a log-phase bacterial culture where death and bacterial breakdown is not prominent. After the incubation, the two fractions (cell wall and supernatant) are prepared. The initial separation is accomplished by decanting the entire culture into a 50 mL vial and centrifugation at 2400 rpm. Bacterial aggregates form a pellet. The supernatant is gently be decanted into a new vial. From this vial, smaller 1 mL samples are aliquoted into Eppendorf vials and subjected to high speed centrifugation, followed by three serial filtrations, to eliminate any intact bacteria and fractions thereof. The sterile, filtered supernatant is aliquoted and multiple aliquots frozen immediately at −80° C. The original pellet from the initial centrifugation is used to prepare the cell wall fraction. The wet pellet is frozen and thawed. The thawed slush is transferred to an Eppendorf vial and washed twice in physiological saline using high speed centrifugation. Then the pellet is transferred to a glass vial and subjected to bead milling using low-protein-binding Zirconium beads with a diameter of 100 micrometer. The milling is performed by repeated 'pulsing' using a Vortex mixer. The beads are removed and the slush containing the broken cell wall fragments are sterile-filtered into multiple aliquots that will be frozen immediately at −80° C.

Biological activity of *Bacillus coagulans* Supernatant and Cell Wall Components In order to identify the molecular weights of predominant protein/carbohydrate compounds in the supernatant and cell wall fractions of BC, Electrophoresis is used to understand the protein and polysaccharide makeup of *Bacillus coagulans* fractions and spores. A typical protein gel electrophoresis method is shown in FIG. 31. This process separates the proteins and polysaccharides by molecular weight and gives a valuable fingerprint for each of the BC fractions. Electrophoretic separation provides information about the relative quantity of specific proteins and polysaccharides in the product.

Figure 32:
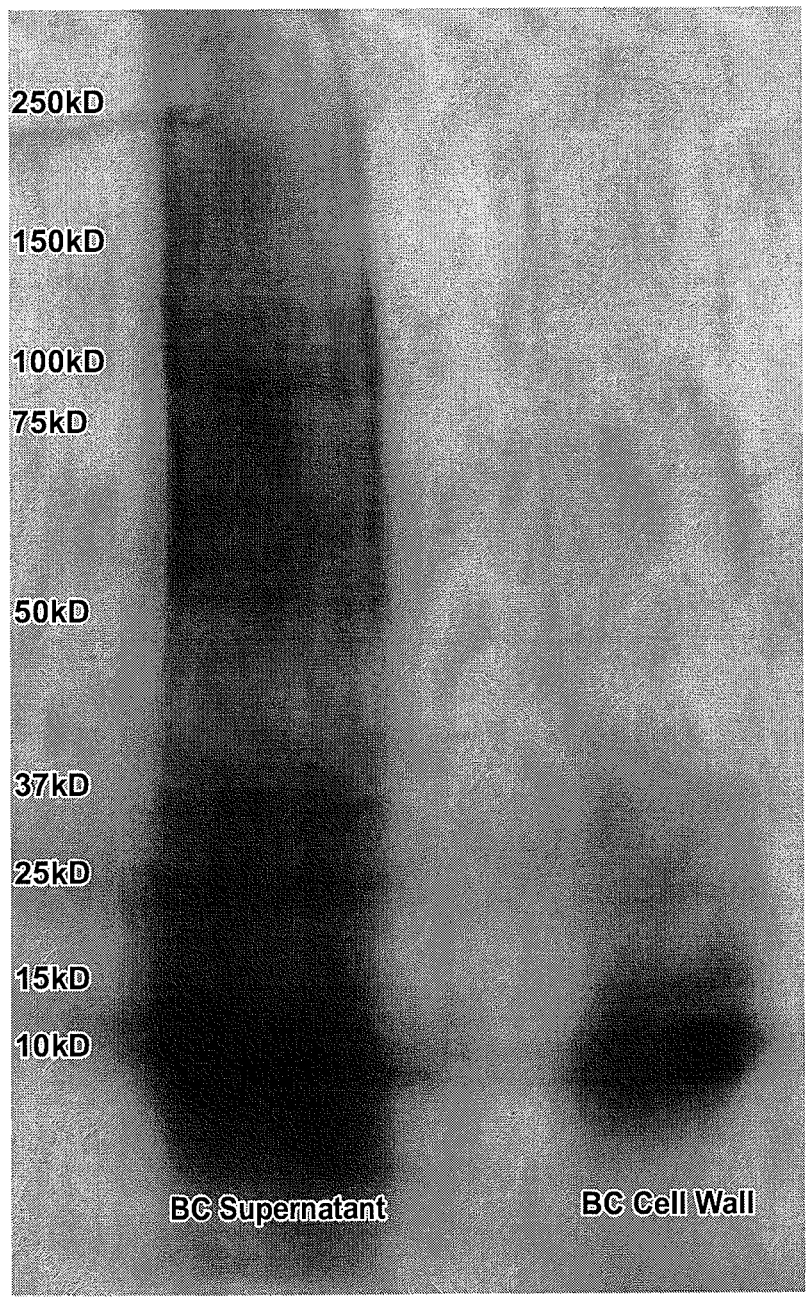
FIG. 32 is a photograph depicting the results of a gel electrophoresis experiment with *Bacillus coagulans* supernatant and cell wall fractions.

Gel electrophoresis of the previous batch of supernatant and cell wall fractions showed several regions of interest. The supernatant contains compounds lower than 5-10 kDa, i.e., lower than the range that can be clearly fractionated by SDS gelelectrophoresis (see, smear below the words "BC Supernatant" in FIG. 32). Both fractions contained double bands in the 10 kDa range. The supernatant contained several additional prominent bands between 20-30 kDa and between 50-150 kDa. Fractionation of the supernatant and the cell wall fraction is carried out to yield three fractions or purified preparations A) Below 3 kDa, B) between 3-30 kDa, and purification C) between 30-200 kDa. The major bioactive compounds from the cell wall are in fraction B. Electrophoresis is used as a tool to ensure product consistency during stages of product development. It is also useful as a regular quality control tool during manufacturing.

Size fractionation by molecular weight (<3, 3-30, 30-200 kDa) of both supernatant and cell wall fractions is performed to further characterize the three main identified biological activities: a) Anti-inflammatory effect, as measured by inhibition of cell migration in response to inflammatory mediators; b) Effect on NK cell activation; and c) Effect on cytokine production.

Anti-Inflammatory Effect: Inhibition of Leukotriene B4 Directed Migration

The PMN cell is a highly active and migratory cell type. *Bacillus coagulans* fractions have strong anti-inflammatory effects when exposed to the known inflammatory cytokine LTB4. Crude BC cell wall and BC supernatant are fractionated into the following molecular weight ranges: a) <3 kDa, b) 3-30 kDa, and c) 30-200 kDa. Similar volumes of *Bacillus coagulans* cell wall and supernatant are placed into centrifugation columns that filter out specific molecular weight fractions. After centrifugation the remaining volumes are serial diluted and placed in with the PMN's before plating into the top chamber.

Figure 33:
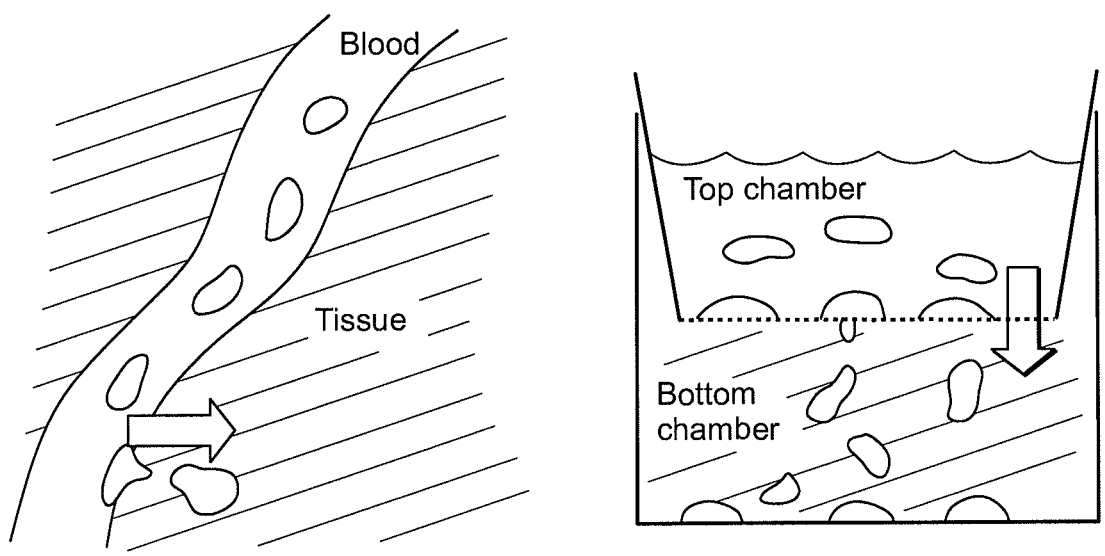
FIG. 33 is a schematic representation of how PMN migration begins in the blood stream and moves into the tissue via transwell migration plates.

Freshly purified PMN cells cultures are set up in double-chamber migration plates, where the bottom chamber mimics tissue, and the top chamber mimics the blood stream as described in FIG. 33. Cells are plated in the top chambers with and without test products, and the different chemo-attractant (LTB4) is present in the bottom chambers. All assays are performed in triplicates, and repeated at least 3 times with consistent results. The testing of migration towards the inflammatory chemo-attractant LTB4 identifies selective responses in this in vitro system, which closely mimics some in vivo models of inflammation, such as rat paw edema. The assay allows a distinction between normal PMN defense mechanisms versus response to inflammation. The anti-inflammatory activity of *Bacillus coagulans* spores is also examined. These assays identify which molecular weight compounds are responsible for the anti-inflammatory effects of BC supernatant and cell wall fractions.

Natural Killer Cell Activation (CD69 Expression)

Crude BC cell wall and BC supernatant are fractionated into the following molecular weight ranges: a) <3 kDa, b) 3-30 kDa, and c) 30-200 kDa. As described above, both BC fractions activated NK cells. Induction of the CD69 activation marker on the NK cells is determined. Freshly purified human peripheral blood mononuclear cells are used for these assays. The cells are plated in 96-well micro-assay plates in triplicate. Negative control wells in triplicate are left untreated. Positive controls are treated with IL-2 at a dose of 100 international units per mL (IU/mL). After 18 hours of culture, cells are stained for the activation molecule CD69 on the surface of CD3-negative, CD56-positive NK cells.

Biological activity of *Bacillus coagulans* supernatant and cell wall components is also assessed after drying and reconstitution to determine if bioactivity is preserved after drying.

This assay identifies which molecular weight compounds are responsible for the NK cell activating effects of BC supernatant and cell wall fractions. The ability of *Bacillus coagulans* spores to activate NK cells is also examined.

Cytokine Production

Crude BC cell wall and BC supernatant are fractionated into the following molecular weight ranges: a) <3 kDa, b) 3-30 kDa, and c) 30-200 kDa. Previous experiments showed that the BC fractions directly induced changes in cytokine production. The fractions will be examined to identify which molecular weight ranges of compounds are responsible for this change in the BC supernatant and cell wall fractions. Freshly purified human peripheral blood mononuclear cells (PBMC) will be cultured in the absence versus presence of serial dilutions of BC fractions. Biological activity of *Bacillus coagulans* supernatant and cell wall components is also assessed after drying and reconstitution to determine if bioactivity is preserved after drying.

The ability of *Bacillus coagulans* spores to induce the production of cytokines IL-2, IL-4, IL-6, IL-10, TNF-alpha, and IFN-gamma is also examined.

EXAMPLE 10

A Controlled Trial to Evaluate the Effects of GBI-30 (GanedenBC$^{30}$) (Viable Cells and Spores) on the Immune System The beneficial effect of GanedenBC$^{30}$ (*Bacillus coagulans* GBI-30, ATCC Designation Number PTA-6086) on the immune system in healthy individuals was evaluated when challenged with the adenovirus and influenza. Studies were also carried out to determine the beneficial effect of GanedenBC$^{30}$ (*Bacillus coagulans* GBI-30, ATCC Designation Number PTA-6086) in health individuals on % CD3CD69 cells—a marker for T-lymphocyte activity.

Ten healthy adult subjects were recruited for this study. No concurrent illness or recent immunization was allowed. Blood was drawn at baseline at day 0. Subjects were instructed to consume 1 capsule daily containing 500 million CFU's of GanedenBC$^{30}$ daily for 30 days. Blood was drawn again on day 30. Due to one subject being statistically different at baseline, only 9 subjects were used in the final analysis.

Blood samples were taken and stimulated with either the adenovirus or influenza A and incubated for 24 hours and then vortexed. 100 microliters of the sample was drawn off and of that 20 microliters were used for the % CD3CD69 testing. 900 microliters from the remaining samples were drawn and centrifuged and the plasma removed. Samples of the plasma were taken and used in the cytokine testing. Various cytokines were tested, and ones with statistically changes are noted below.

When 500 million CFU/day were consumed, the immune system of subjects was boosted when challenged both with the adenovirus and influenza A. The % CD9CD69 cells, were increased after demonstrating an ability to increase T-lymphocyte activity. Statistically significant changes were seen in IL-8 production (P=0.039) when exposed to influenza A, and INF-γ production (P=0.039) when exposed to adenovirus. Statistically significant increases in % CD3CD69 (P=0.023) were seen both to adenovirus and influenza A.

These data indicate that a probiotic composition containing 2 billion CFU of GanedenBC$^{30}$, when consumed daily, boosted the immune system. When consumed at only 500 million CFU/day, the composition was able to demonstrate statistically significant boosts to the immune system as well as increasing T-lymphocyte activity.

Other embodiments are within the scope and spirit of the invention. It will be recognized by a person of ordinary skill in the art that various components of the examples described herein can be interchanged and/or substituted with various components in other examples, and that other modifications may be possible. To the extent that any of the material incorporated by reference herein conflicts with the terms of the present disclosure, the present disclosure is intended to be controlling. Further, while the description above refers to the invention, the description may include more than one invention.

What is claimed is:

1. A method of enhancing an immune response to a microbial pathogen in a subject comprising:
    identifying a subject infected with said microbial pathogen; and
    administering to said subject a composition comprising dried or lyophilized cell wall components of *Bacillus coagulans* and dried supernatant of *Bacillus coagulans* in an amount that enhances said immune response.

2. The method of claim 1, wherein said microbial pathogen is a bacterium or a virus.

3. The method of claim 1, wherein said microbial pathogen causes a viral respiratory infection.

4. The method of claim 1, wherein said microbial pathogen comprises an influenza virus.

5. The method of claim 1, wherein said microbial pathogen comprises a human, an avian, or a swine influenza virus, or a combination thereof.

6. The method of claim 1, wherein said microbial pathogen comprises an adenovirus.

7. The method of claim 1, wherein enhancement of said immune response comprises an increase in cytokine production or an increase in immune cell migration to an infection site.

8. The method of claim 7, wherein said cytokine comprises interleukin-2(IL-2), IL-4, IL-6, IL-10, tumor necrosis factor -a (TNF-a), or interferon- y (IFN-y).

9. The method of claim 1, wherein enhancement of said immune response comprises increasing cytokine production, activating immune surveillance aspect of polymorphonuclear leukocytes (PMN), increasing immune cell chemotaxis, activating natural killer (NK) cells, or increasing monocyte phagocytosis.

10. The method of claim 9, wherein enhancement of said immune response comprises increased phagocytosis or chemotaxis by said PMNs.

11. The method of claim 9, wherein enhancement of said immune response comprises increased expression of CD69 on said NK cells.

12. The method of claim 1, wherein said *Bacillus coagulans* is *Bacillus coagulans* hammer strain Accession No. ATCC 31284.

13. The method of claim 1, wherein said *Bacillus coagulans* is selected from the group consisting of GBI-30 strain (ATCC Designation Number PTA-6086), GBI-20 strain (ATCC Designation Number PTA-6085), and GBI-40strain (ATCC Designation Number PTA-6087).

14. The method of claim 1, wherein said composition is in the form of a powder.

15. The method of claim 1, wherein said dried composition is reconstituted in water or other aqueous solution prior to use.

* * * * *